United States Patent [19]

Albert et al.

[11] Patent Number: 4,814,346

[45] Date of Patent: Mar. 21, 1989

[54] BENZOPYRANS AND USE THEREOF IN TREATING VASCULAR DISEASES

[75] Inventors: Alban I. Albert, Grand-Saconnex, Switzerland; Friedrich W. Zilliken, Remagen, Fed. Rep. of Germany

[73] Assignee: Zyma SA, Nyon, Switzerland

[21] Appl. No.: 116,737

[22] Filed: Nov. 4, 1987

[30] Foreign Application Priority Data

Nov. 4, 1986 [GB] United Kingdom ............... 8626344

[51] Int. Cl.$^4$ .................... A61K 31/35; C07D 311/04; C07D 493/00
[52] U.S. Cl. .................................. 514/454; 514/456; 549/406; 549/387
[58] Field of Search ............... 549/332, 359, 407, 408, 549/406, 387; 514/452, 458, 460, 454, 456

[56] References Cited

U.S. PATENT DOCUMENTS

| | | | |
|---|---|---|---|
| 3,813,415 | 5/1974 | Kycia et al. | 549/322 |
| 4,157,985 | 6/1979 | Zilliken | 549/332 |
| 4,218,489 | 8/1980 | Zilliken | 549/332 |
| 4,232,122 | 11/1980 | Zilliken | 549/332 |
| 4,234,577 | 11/1980 | Zilliken | 549/332 |
| 4,264,509 | 4/1981 | Zilliken | 549/332 |
| 4,368,264 | 1/1983 | Zilliken | 549/332 |

FOREIGN PATENT DOCUMENTS

| | | | |
|---|---|---|---|
| WO80/02027 | 10/1980 | PCT Int'l Appl. | 549/332 |
| WO-A-80/2098 | 10/1980 | PCT Int'l Appl. | 514/454 |

OTHER PUBLICATIONS

Kuhl et al., Prostaglandins, vol. 28, No. 6, pp. 783–804 (Dec. 1984).
Jha et al., Biochem. Pharmacology, vol. 34, No. 9, pp. 1367–1369 (1985).
Ingham et al., Phytochemistry, vol. 18, pp. 1711–1714 (1979).
Chemical Abstracts, vol. 92, p. 177, No. 177383c (1980).
Chemical Abstracts, vol. 82, p. 504, No. 111965f (1975).
Chemical Abstracts, vol. 79, p. 217, No. 63542e (1973).
Ingham et al., Chem. Abstr. vol. 92 (1980) p. 326, 177383C.
Kramer et al., Phytochemistry, vol. 23, No. 10, pp. 2203–2205 (1984).
Lamberton et al., Aust. J. Chem. 1978, 31, pp. 455–457.
Chemical Abstracts, vol. 70, p. 339, No. 77837f (1969).
Campbell et al., J. Chem. Soc. (C), 13, pp. 1787–1795 (1969).
Szabo et al., Acta. Chem. Acad. Sci. Hung. 90(4), pp. 381–393 (1976).
Inoue, Bull. Chem. Soc. Japan, vol. 37, No. 5, pp. 601–605 (1964).
Szabo et al., Tetrahedron Letters, No. 19, pp. 1659–1662 (1973).

*Primary Examiner*—Mary C. Lee
*Assistant Examiner*—Robert C. Whittenbaugh
*Attorney, Agent, or Firm*—Wenderoth, Lind & Ponack

[57] ABSTRACT

Isoflavans of the formula I wherein the groups OR, R', R'' and ring B are as defined in the specification, exhibit valuable pharmacological properties, especially for the treatment of vascular diseases. They are prepared by methods known per se.

13 Claims, No Drawings

BENZOPYRANS AND USE THEREOF IN TREATING VASCULAR DISEASES

The present invention relates to isoflavans (=3,4-dihydro-3-phenyl-2H-1-benzopyrans) of the formula I

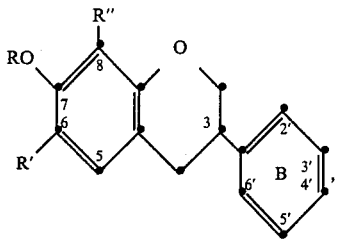

wherein the group OR represents hydroxy; lower alkoxy which is unsubstituted or substituted by hydroxy, lower alkoxy, amino, lower alkylamino, di-lower alkylamino, carboxy or lower alkoxycarbonyl; or lower alkanoyloxy; one of the radicals R' and R" represents hydroxy, lower alkoxy, lower alkanoyloxy or lower alkyl and the other one is hydrogen; or the groups OR and R' together form a bivalent methylenedioxy radical which is unsubstituted or substituted by lower alkyl and/or phenyl, and R" is hydrogen; or the groups OR and R" together form a bivalent methylenedioxy radical which is unsubstituted or substituted by lower alkyl and/or phenyl, and R' is hydrogen; and the ring B is unsubstituted or substituted by lower alkyl, phenyl-lower alkyl, diphenyl-lower alkyl, phenyl, lower alkanoyloxy, halogen, amino, lower alkylamino, di-lower alkylamino, phenylamino, lower alkanoylamino, benzoylamino; lower alkylsulfonylamino, phenylsulfonylamino; lower alkanoyl, benzoyl, carboxy, lower alkoxycarbonyl, carbamoyl, N-lower alkylcarbamoyl, N,N-di-lower alkylcarbamoyl, cyano, ureido, N-lower alkylureido, lower alkylsulfonyl; phenylsulfonyl; lower alkyl which is substituted by hydroxy, lower alkoxy, amino, lower alkylamino, di-lower alkylamino, halogen, carboxy or lower alkoxycarbonyl; lower alkoxy which is substituted by hydroxy, lower alkoxy, amino, lower alkylamino, di-lower alkylamino, halogen, carboxy or lower alkoxycarbonyl; $C_3$-$C_7$-alkoxy; and/or bivalent methylenedioxy;

or wherein the ring B is monosubstituted by hydroxy, methoxy or ethoxy, provided that R' is other than hydroxy, methoxy or ethoxy, if the group OR represents hydroxy, methoxy or ethoxy; or wherein the ring B is disubstituted by methoxy and lower alkoxy, provided in case of 2',4'-dimethoxy substitution that R' and R" are other than methoxy, if the group OR represents methoxy; with the proviso that the ring B must be substituted, if R' is hydroxy and the group OR represents hydroxy or methoxy; it being possible for all phenyl groups mentioned as such or in composed radicals (like benzoyl, phenylamino etc.) to be unsubstituted or substituted by lower alkyl, lower alkoxy, halogen, hydroxy and/or nitro; and salts thereof, processes for the manufacture of these compounds, pharmaceutical compositions comprising said compounds, and their use for the manufacture of pharmaceutical preparations or as pharmacologically active compounds.

The general definitions used herein have the following meanings within the scope of the present invention.

The term "lower" means that groups so defined have preferably up to and including 7, especially up to and including 4, carbon atoms.

Lower alkyl as such or in composed radicals like lower alkoxy etc. is e.g. n-propyl, isopropyl, n-butyl, isobutyl, sec.-butyl, tert.-butyl, n-pentyl, isopentyl, neopentyl, n-hexyl, isohexyl or n-heptyl, preferably ethyl and especially methyl.

Lower alkyl substituted by halogen is preferably trifluoromethyl.

Lower alkanoyl as such or in composed radicals like lower alkanoyloxy etc. is e.g. formyl, acetyl, propionyl, n-butyryl, pivaloyl or valeroyl.

Halogen is preferably fluoro or chloro, but may be also bromo or iodo.

Phenylsulfonylamino means the radical —NH—$SO_2C_6H_5$, lower alkylsulfonyl is —$SO_2$—lower alkyl.

Ureido and lower alkylureido represent the radicals —NH—$CONH_2$ and —NH—CONHAlk (3-alkylureido) or —NAlk—$CONH_2$ (1-alkylureido) respectively (Alk=lower alkyl).

In lower alkoxy radicals which are substituted by hydroxy, epoxy, lower alkoxy, amino, lower alkylamino, di-lower alkylamino or halogen, the substituents mentioned are normally separated from the oxy group in lower alkoxy by at least two carbon atoms.

Salts are preferably pharmaceutically acceptable salts, especially metal or ammonium salts of said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium hydroxides, e.g., methylamine, diethylamine, dicyclohexylamine, triethanolamine, ethylenediamine, tris-(hydroxymethyl)aminomethane or benzyltrimethylammonium hydroxide. Said compounds of formula I having a basic group form acid addition salts of preferably the pharmaceutically acceptable inorganic or organic acids, such as of strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid, or other acidic organic substances, such as ascorbic acid.

For the purposes of isolation or purification it is also possible to use pharmaceutically unacceptable salts. Only the pharmaceutically acceptable, non-toxic salts are used therapeutically, however, and these are therefore preferred.

The compounds of this invention exhibit valuable pharmacological properties. They, for example, improve hemorheological parameters, inhibit platelet aggregation and phosphodiesterase, have calcium antogonist activity and improve peripheral oxygenation. These properties make the compounds useful, e.g. for the treatment of vascular diseases as for example, intermittent claudication, artherosclerosis, thrombotic diseases, myocardial ischemia, myocardial infarct, coronary diseases, cerebral ischemia, cerebral infarct, diabetic microangiopathy, arterial ulcer, Raynaud's syndrom, vasospasm, chronic venous insufficiency, venous ulcer or haemorrhoids.

Furthermore, the compounds of the invention are inhibitors of the 5-lipoxygenase and/or 12-lipoxygenase and have antioxydative activity. These properties make the compounds useful e.g. for the treatment of inflammatory diseases, hypersensitization and asthma as well as skin diseases, e.g. psoriasis.

(1) Hemorheological parameters

The improvement of hemorheology parameters can be e.g. demonstrated with in vitro pharmacological models of human blood. In a first model, the analysis of the flow behaviour of concentrated suspensions of washed erythrocytes is described and measured according to TEITEL [Blood Cells, 3, 55–70 (1977)] and SCHMID and SCHOENBEIN [VASA, 4, 263–270 (1975)]. In a second model, the hemorheological improvement is analysed with the yield shear stress technique according to KIESEWETTER et al. [Biblthca. haemat. 47, 14–20 (1981)] and KIESEWETTER et al. [Biorheology, 19, 363–374 (1982)]. Results are obtained by calculating ED50 in μM (concentration of substance which improves hemorheologic alteration by 50% due to Ca++ stress). The ED50 values are, in the case of the compounds of the invention, approximately 0.05 μM or above.

(2) cAMP-phosphodiesterase inhibition activity

The inhibitory effect of the compounds of the invention on cAMP-phosphodiesterase activity can be e.g. obtained according to WELLS et al. [Biochim. Biophys. Acta 384, 430–432 (1975)] and BERETZ et al. [Biochem. Pharmacol. 35, 257–262 (1986)]. Phosphodiesterases are obtained from fresh human platelets or fresh human aorta. The effect of the compounds on cAMP-phosphodiesterase of fresh human tissue is studied by adding solutions of compounds to be tested from 1 to 100 μM. IC50 values (concentration which is necessary to inhibit 50% of the reaction) can be determined in order to evaluate the activity of the compounds. They are approximately 1 μM or above in the case of the compounds of the invention.

(3) Inhibition of platelet aggregation

The inhibition of platelet aggregation can be e.g. demonstrated with the pharmacological model of washed human platelet collected from a forearm vein. Washed platelet suspensions are prepared according to CAZENAVE et al. [Ann. Biol. Clin. 41, 167 (1983)] and BERETZ et al. [Biochem. Pharmacol. 35, 257–262 (1986)]. Results can be obtained by calculating IC50 (concentration of the compound which inhibits 50% of platelet aggregation). The IC50 values are, in the case of the compounds of the invention, approximately 1 μM or above.

(4) Calcium antagonist activity

The evaluation of the property to inhibit the contraction induced by calcium chloride or potassium chloride depolarized rat mesentery can be made e.g. using the method described by BROCKAERT and GODFRAIND [Eur. J. Pharmacol. 53, 281 (1979)]. The inhibitory effect of the compounds is expressed as the concentration necessary to inhibit 50% of the initial contraction obtained with $CaCl_2$.

(5) Peripheral oxygenation

The effect of the compounds on peripheral oxygenation can be measured e.g. according to SUNDERPLASSMANN [Angiology, 32, 686–698 (1981)] and HAUSS [in "Oxyg. Transp. tissue in Experimental Biology and Medicine", Silver Ed. 1978, 419–422]. A $pO_2$ mean can be calculated after oral administration and compared between control and treated series of rats. A comparison of $pO_2$ can be realised between pretreatment and posttreatment values for the intravenous administration.

(6) Inhibition of the 5-lipoxygenase pathway

The inhibition of the 5-lipoxygenase can be e.g. demonstrated according to KUHL et al. [Prostaglandins 28, 783–804 (1984)]. Procine peripheral blood leucocytes are used in order to test the effect of the compounds of the invention. These effects are studied by adding solutions of the compounds to be tested of 0.1 to 1000 μM. IC50 values (concentration of the compound which inhibits 50% of the 5-lipoxygenation) can be calculated in order to evaluate and compare the activity of the compounds. The IC50 values are lying, for the compounds of the invention, approximately between 0.35 and 200 μM or above.

(7) Inhibition of the 12-lipoxygenase pathway

The inhibitory effect of the compounds of the invention related to the 12-lipoxygenase activity can be e.g. demonstrated according to KUHL et al. [Prostaglandins 28, 783–804 (1984)]. Porcine peripheral blood leucocytes are used for compounds evaluation. Solutions of the compounds to be tested are added with a final concentration of 0.1 to 1000 μM. Results are expressed as IC50 values (concentration of the compound which inhibits 50% of the 12-lipoxygenation). For the compounds of the invention, IC50 values are lying approximately between 1 and 200 μM or above.

(8) Antioxydative activity

The antioxydative activity can be e.g. demonstrated using the active oxygen method (AOM) according to WHEELER, Oil and Soap 9, 89 (1932). Stripped lard is used for estimation of the oxydative capacity of the compounds. A temperature stimuli (60° C. for three days) is applied before tritration with $Na_2S_2O_3$. The effect of the compounds on antioxydation activity is studied by adding a solution of the compound to be tested of 25 to 500 ppm (equivalent of 25 μg of compound/2 g lard to 500 μg of compound/2 g lard). Results are expressed as IC50 values (concentration of the compound inhibiting 50% of the oxydation reaction). For the compounds of the invention, IC50 values are lying approximately in the range of 0.06 to 2.30 μM or above.

Preferred are the isoflavans of the formula I, wherein the group OR represents hydroxy, lower alkoxy or lower alkanoyloxy; one of the radicals R' and R" represents hydroxy, lower alkoxy, lower alkanoyloxy or lower alkyl and the other one is hydrogen; or the groups OR and R' together form a bivalent methylenedioxy radical which is unsubstituted or substituted by lower alkyl and/or phenyl, and R" is hydrogen; or the groups OR and R" together form a bivalent methylenedioxy radical which is unsubstituted or substituted by lower alkyl and/or phenyl, and R' is hydrogen; and the ring B is unsubstituted or substituted by lower alkyl, lower alkanoyloxy, halogen, amino, lower alkylamino, di-lower alkylamino, phenylamino, lower alkanoylamino, benzoylamino; lower alkylsulfonylamino, phenylsulfonylamino; lower alkanoyl, benzoyl, carboxy, lower alkoxycarbonyl, carbamoyl, N-lower alkylcarbamoyl, N,N-di-lower alkylcarbamoyl, cyano, lower alkylsulfonyl; phenylsulfonyl; lower alkyl which is substituted by halogen, carboxy or lower alkoxycarbonyl; lower alkoxy which is substituted by carboxy or lower alkoxycarbonyl; or bivalent methylenedioxy;

or wherein the ring B is monosubstituted by hydroxy or methoxy, provided that R' is other than hydroxy, methoxy or ethoxy, if the group OR represents hydroxy, methoxy or ethoxy; or wherein the ring B is disubstituted by methoxy, provided in case of 2',4'-dimethoxy substitution that R' and R" are other than methoxy, if the group OR represents methoxy; with the proviso that the ring B must be substituted, if R' is hydroxy and the group OR represents hydroxy or methoxy; and pharmaceutically acceptable salts thereof.

Particularly preferred are the isoflavans of the formula I, wherein the group OR represents hydroxy, lower alkoxy or lower alkanoyloxy; one of the radicals R' and R" represents hydroxy, lower alkoxy, lower alkanoyloxy or lower alkyl and the other one is hydrogen; or the groups OR and R' together form a bivalent methylenedioxy radical which is unsubstituted or disubstituted by phenyl, and R" is hydrogen; or the groups OR and R" together form a bivalent methylenedioxy radical which is unsubstituted or disubstituted by phenyl, and R' is hydrogen; and the ring B is unsubstituted or substituted by lower alkyl, lower alkanoyloxy, halogen, amino, lower alkanoylamino, phenylsulfonylamino; carboxy, lower alkoxycarbonyl, carbamoyl, lower alkylsulfonyl; lower alkyl which is substituted by halogen or carboxy; lower alkoxy which is substituted by carboxy or lower alkoxycarbonyl; or bivalent methylenedioxy;

or wherein the ring B is monosubstituted by hydroxy or methoxy, provided that R' is other than hydroxy, methoxy or ethoxy, if the group OR represents hydroxy, methoxy or ethoxy; or wherein the ring B is disubstituted by methoxy, provided in case of 2',4'-dimethoxy substitution that R' and R" are other than methoxy, if the group OR represents methoxy;

with the proviso that the ring B must be substituted, if R' is hydroxy and the group OR represents hydroxy or methoxy; and pharmaceutically acceptable salts thereof.

Especially preferred are the isoflavans of the formula I, wherein the group OR represents hydroxy; lower alkoxy or lower alkanoyloxy; one of the radicals R' and R" represents hydroxy, lower alkoxy, lower alkanoyloxy or lower alkyl and the other one is hydrogen; or the groups OR and R' together form a bivalent methylenedioxy radical which is unsubstituted or disubstituted by phenyl, and R" is hydrogen; or the groups OR and R" together form a bivalent methylenedioxy radical which is unsubstituted or disubstituted by phenyl, and R' is hydrogen; and the ring B is unsubstituted or substituted by lower alkyl, lower alkanoyloxy, halogen, amino, lower alkylamino, di-lower alkylamino, or lower alkoxy which is substituted by carboxy or lower alkoxycarbonyl; or ring B is 3,4-dimethoxy-substituted;

with the proviso that the ring B must be substituted, if R' is hydroxy and the group OR represents hydroxy or methoxy; and pharmaceutically acceptable salts thereof.

Subgroups of the compounds of the invention are represented by (a) the compounds of formula I which are 7,8-disubstituted, i.e. wherein R' represents hydrogen;
(b) the compounds of the formula I which are 6,7-disubstituted, i.e. wherein R" represents hydrogen; and
(c) the compounds of the formula I wherein the ring B is substituted as defined above with the exclusion of all hydroxy, lower alkoxy and methylenedioxy substituents (but is not unsubstituted).

In particular preferred are the compounds of formula I, wherein the ring B is unsubstituted, monosubstituted in 3- or 4-position by one of the substituents mentioned or disubstituted in 3- and 4-position by methoxy. Especially preferred are the compounds of the formula I, wherein the ring B is monosubstituted in 4-position.

Above all are preferred the compounds of formula I described in the examples and pharmaceutically acceptable salts thereof.

The compounds of the formula I can be produced by processes known per se, e.g.

(a) by reducing a compound of the formula II

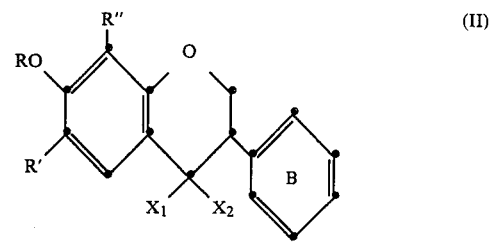

wherein the group $CX_1X_2$ represents a carbonyl group and the dotted line represents a bond or no bond, or wherein $CX_1X_2$ represents a hydroxymethylene group and the dotted line represents no bond, and OR, R', R" and ring B are as defined under formula I or represent radicals which are convertible to the groups OR, R', R" and/or ring B as defined under formula I by reduction, optionally with simultaneous reduction occurring within the groups OR, R', R" and/or ring B, or (b) by reducing a compound of the formula III

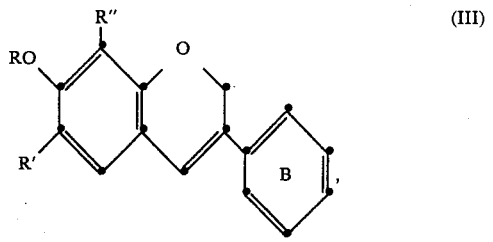

wherein OR, R', R" and ring B are as defined under formula I or represent radicals which are convertible to the groups OR, R', R" and/or ring B is defined under formula I by reduction, optionally with simultaneous reduction occurring within the groups OR, R', R" and/or ring B, or (c) by reducing a compound of the formula IV

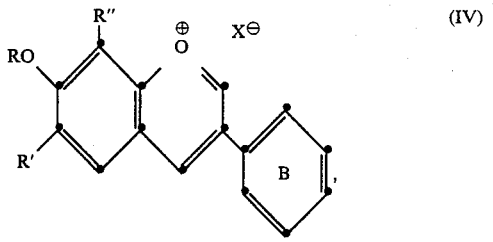

wherein OR, R', R" and ring B are as defined under formula I or represent radicals which are convertible to the groups OR, R', R" and/or ring B as defined under formula I by reduction, and $X^{\ominus}$ is an anion, optionally with simultaneous reduction occurring within the groups OR, R', R" and/or ring B, or (d) by reducing a compound of the formula V

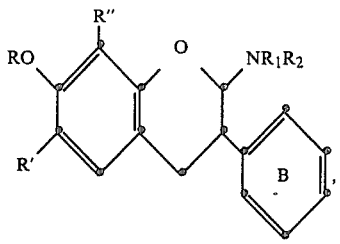

wherein the group $NR_1R_2$ represents a tertiary amino group and OR, R', R" and ring B are as defined under formula I or represent radicals which are convertible to the groups OR, R', R" and/or ring B as defined under formula I by reduction, optionally with simultaneous reduction occurring within the groups OR, R', R" and/or ring B;

and/or, if desired, converting a resulting compound of formula I into another compound of formula I, and/or converting a resulting salt into the free compound or into another salt, and/or converting a resulting free compound of the formula I having salt-forming properties into a salt, and/or separating a resulting mixture of stereoisomers or optical isomers, such as a diastereoisomeric mixture, into the individual stereoisomers, optical isomers or enantiomeric mixtures, respectively, and/or splitting enantiomeric mixtures, such as a racemate, into the optical isomers.

Process (a):

The reduction can be accomplished e.g. with hydrogen in the presence of a hydrogenation catalyst, preferably Pd/C, and also e.g. platinum or platinum dioxide, optionally in the presence of a promoter, e.g. an acid, such as an inorganic acid, e.g. $H_2SO_4$, HCl or $HClO_4$, an organic carboxylic acid, e.g. acetic acid or trifluoroacetic acid, or an organic sulfonic acid, e.g. phenylsulfonic acid, p-toluenesulfonic acid or methanesulfonic acid, optionally in the presence of an inert aprotic or protic solvent, or mixtures thereof, and at a hydrogen pressure of 1 to 50 bar [cp. Szabo et al., Acta Chim. Acad. Sci. Hung. 90, 381 (1976); Bull. Chem. Soc. Japan 37, 601, 606 (1964); Aust. J. Chem. 31, 455 (1978); Tetrahedron Lett. 1973, 1659].

Another possibility to reduce the compounds of formula II wherein $CX_1X_2$ represents carbonyl and the dotted line is a bond, the isoflavone intermediates of formula IIa,

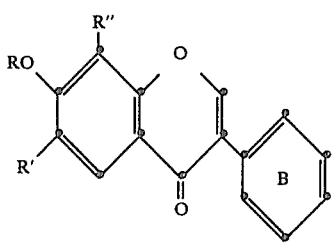

wherein OR, R', R" and ring B are as defined under formula I, is given by the Clemmensen reduction, i.e. with amalgamated zinc, concentrated HCl and optionally e.g. acetic acid [cp. Bull. Chem. Soc. Japan 37, 601, 606 (1964)].

The isoflavones of formula IIa can be produced by processes known per se, e.g. by (1) reacting a compound of formula VI

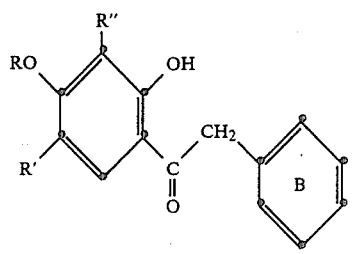

wherein OR, R', R" and ring B are as defined under formula I, with a derivative of formic acid under cyclization conditions, or (2) reacting a compound of formula VIII

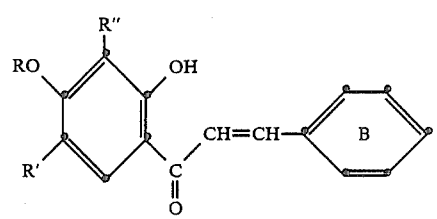

wherein OR, R', R" and ring B are as defined under formula I, with an agent suitable for forming the isoflavone by oxidative rearrangement and cyclization.

Process 1:

The reaction consists of the condensation of the activated $CH_2$ group of the compound of formula VI with a derivative of formic acid followed by cyclization. Useful formic acid derivatives are e.g. dimethylformamide, triethyl orthoformate or ethyl formate. Cyclization agents that can be used are e.g. methanesulfonyl chloride/boron trifluoride etherate (cp. J.C.S. Chem. Comm. 1976, 78), $POCl_3$ [cp. C.A. 81, 135890h (1974) and C.A. 81, 25496b (1974)], pyridine and piperidine [cp. Indian J. Chem. 15B, 238 (1977); C.A. 87, 22970q (1977)], $HClO_4$, [cp. J. Chem. Res. (S) 1978, 47] or sodium [cp. Bull. Chem. Soc. Jap. 53, 831 (1980); Indian J. Chem. 6, 485 (1968)].

The intermediates of formula VI can be prepared e.g. by reacting a phenol of formula XII

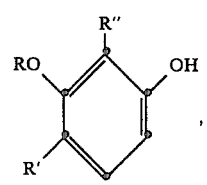

wherein OR, R' and R" are as defined under formula I, with a phenylacetic acid derivative of the formula XIII

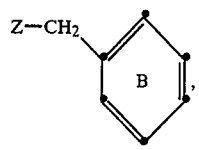

wherein Z preferably is cyano or halocarbonyl, especially —COCl, and the ring B is as defined under formula I, in the presence of a Lewis acid catalyst, e.g. a metal halide, such as $ZnCl_2$, $AlCl_3$ or $FeCl_3$, in a Houben-Hoesch or Friedel-Crafts acylation reaction, respectively [cp. Merck Index, 10th Edition, ONR 46 and 33].

Another possibility to obtain the compounds of formula VI is e.g. the Fries rearrangement [cp. Merck Index, 10th Edition, ONR 33] which comprises the reaction of a compound of formula XII as defined above with a compound of formula XIII, wherein Z represents halocarbonyl, in the absence of any Lewis acid catalyst resulting in the corresponding phenolic ester which rearranges under treatment with one of the Lewis acid catalysts mentioned above to the ortho-phenolic ketones of formula VI.

The novel isoflavones of the formula IIa

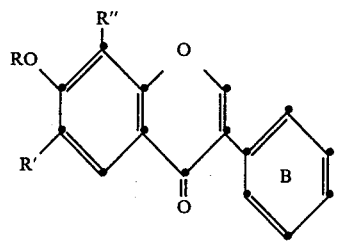

wherein OR, R', R" and ring B are as defined under formula I, are valuable intermediates for the prepration of the therapeutically active isofavans of the formula I and thus form another embodiment of the present invention.

Especially preferred as intermediates are the novel isoflavones of the formula IIa described in the examples.

Process 2:

The cyclizaton is achieved either in the presence of thallium(III) salts, e.g. $Tl(NO_3)_3$ or $Tl(acetate)_3$ [cp. J. Chem. Soc. Perkin Tr. 1 1974, 305; J. Chem. Soc. (C) 1970, 125 or Gazz. Chim. Ital. 112, 289 (1982)] or e.g. with the aid of hydrazoic acid [cp. Ann. Ist. Super. Sanita (1973), 9, Pt. 2-3, 174–175]. The starting materials of formula VIII can be prepared e.g. by condensation of the corresponding ortho-hydroxy-acetophenone with an optionally substituted benzaldehyde e.g. in the presence of a base, such as NaOH or KOH.

The compounds of the formula II, wherein $CX_1X_2$ represents carbonyl and the dotted line is no bond, the isoflavanone intermediates of formula IIb,

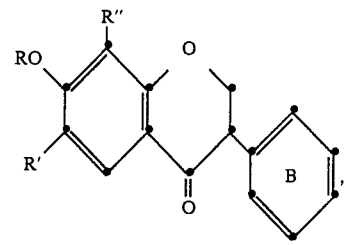

can be prepared e.g. by selectively reducing the double bond in an isoflavone intermediate of the formula IIa, e.g. with hydrogen and a Pd/C catalyst in the presence of a tertiary amine, e.g. triethylamine; or with $H_2//Pd/C$ in dioxane, or with $H_2//Pd/C$ in an aqueous ethanolic buffer pH 9-10 [cp. Szabo et al., Acta Chim. Acad. Sci. Hung. 90, 381 (1976)].

The compounds of formula II wherein $CX_1X_2$ represents hydroxymethylene and the dotted line is no bond, the isoflavanol intermediates of formula IIc,

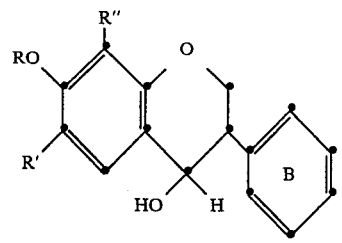

can be prepared e.g. by selectively reducing an isoflavone of formula IIa or an isoflavanone of formula IIb, e.g. with hydrogen and Raney nickel; or with $H_2//Pd/C$ in ethanol, or with $H_2//Pd/C$ in an aqueous ethanolic buffer pH 3-9 [cp. Szabo et al., loc. cit.].

Process (b):

The reduction according to process (b) is accomplished e.g. by applying the same reduction means as listed above for process (a), preferably by the use of $H_2//Pd/C$. The starting materials of formula III can be prepared e.g. by selective reduction of the carbonyl group in a corresponding coumarine, e.g. with $KBH_4$ [cp. Tetrahedron Lett. 24, 3993 (1983)]. Another possibility is given by reacting a compound of formula IIc first with an acetylating agent, e.g. acetic acid, and then eliminating acetic acid [cp. Bull. Chem. Soc. Jap. 37, 606 (1964)].

Process (c):

The anion $X^\ominus$ can be e.g. the anion of any strong inorganic or organic acid, e.g. halide, such as chloride. The reduction according to process (c) can be performed e.g. by applying the same reduction means as listed above for process (a), preferably by the use of $H_2/Pt//Pd/C$. The starting isoflavylium salts of formula IV can be obtained e.g. by reaction of a compound of formula XII with an optionally substituted 2-phenyplmalondialdehyde under acidic conditions, e.g. in the presence of HCl [cp. Austr. J. Chem. 34, 2647 (1981)].

Process (d):

The group $NR_1R_2$ represents preferably N,N-di-lower alkylamino, N-piperidino, N-piperazino and especially N-morpholino. The reduction according to process (d) is accomplished e.g. by applying the same reduction means as listed above for process (a), preferably H₂//Pd/C. The starting materials of formula V can be prepared e.g. by reacting a corresponding salicylaldehyde with an optionally substituted 2-tert. aminostyrene under heating [cp. J. Chem. Soc. Perkin Trans. 1 1982, 1193].

If any intermediates mentioned contain interfering reactive groups, e.g. carboxy, hydroxy, amino or mercapto groups, such may advantageously be temporarily protected at any stage with easily removable protecting groups. The choice of protecting groups for a particular reaction depends on several factors, e.g. the nature of the functional group to be protected, the structure and stability of the molecule of which the substituent is the functional group, and the reaction conditions. Protecting groups that meet these conditions and their introduction and removal are known to the art and are described, for example, in J. F. W. McOmie, "Protective Groups in Organic Chemistry", Plenum Press, London, New York 1973.

Depending upon the reaction conditions, the compounds of formula I are either obtained in the free form, or as a salt thereof. Any resulting base can be converted into a corresponding acid addition salt, preferably with the use of a therapeutically useful acid or an anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. On the other hand, compounds of formula I containing acidic groups, e.g. carboxy or a phenolic hydroxy group, can be converted into salts in a manner known per se by treating with a base, e.g. an alkali metal hydroxide or alkoxide, an alkali metal or alkaline-earth metal salt, e.g. sodium hydrogen carbonate, ammonia or a suitable organic amine. The free compounds can be obtained by treating such salts with an acid. In view of the close relationship between the free compounds and the compounds in the form of their salts, whenever a compound is referred to in this context, a corresponding salt is also intended, provided such is possible or appropriate under the circumstances.

The compounds of formula I contain at least one asymmetric carbon atom in position 3 and can be found as R- or S-enantiomers as well as enantiomeric mixtures thereof, such as a racemate. The present invention is intended to include all these forms, also those further isomers, and mixtures of at least two isomers, for example a diastereoisomeric mixture or enantiomeric mixture, which become possible if one or more further asymmetric center(s) are present within the molecule.

Any resulting mixtures of diastereoisomers, mixtures of racemates or geometric isomers can be separated on the basis of the physicochemical differences of the constituents, in known manner, into single diastereoisomers, racemates, or geometric isomers, for example by chromatography and/or fractional crystallisation.

Any resulting enantomeric mixtures, such as racemates, can be resolved into the optical isomers (antipodes) by known methods, for example by recrystallisation from an optically active solvent, or with the aid of microorganisms, or by e.g. reacting an acidic end product with an optically active base that forms salts with the racemic acid, and separating the salts obtained in this manner, for example by fractional crystallization, into the diastereoisomeric salts from which the optically active carboxylic acid antipodes can be liberated on acidification.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, e.g. in a temperature range from −20° to +200° C., preferably between room temperature and the boiling point of the solvents used, and at atmospheric or super-atmospheric pressure. The preferred solvents, catalysts and reaction conditions are set forth in the appended illustrative examples.

The compounds, including their salts, can also be obtained in the form of their hydrates, or include other solvents used for their crystallization.

The invention further includes any variant of the present processes, in which an intermediate product obtainable at any stage thereof is used as starting material and the remaining steps are carried out, or the process is discontinued at any stage thereof, or in which a starting material is formed under the reaction conditions, or in which a reaction component is used in the form of a salt or an optically pure antipode. Mainly those starting materialls should be used in said reactions, that lead to the formation of those compounds indicated above as being especially useful. The invention also relates to novel starting materials and processes for their manufacture.

The pharmacologically acceptable compounds of the present invention can be used e.g. for the manufacture of pharmaceutical preparations that contain an effective amount of the active ingredient alone or together with inorganic or organic, solid or liquid, pharmaceutically acceptable carriers. The pharmaceutical preparations are e.g. for enteral, such as oral or rectal, topical, transdermal and parenteral, such as intraperitoneal, intramuscular or intravenous, administration to warm-blooded animals including humans.

For oral administration there are used e.g. tablets or gelatine capsules that contain the active ingredient together with diluents, e.g. lactose, dextrose, sucrose, mannitol, sorbitol and/or celluose, and lubricants, e.g. silica, talc, stearic acid or salts thereof, such as magnesium or calcium stearate, and/or polyethylene glycol; tablets also contain binders, e.g. starches, such as maize, wheat, rice or arrowroot starch, gelatine, tragacanth, methylcellulose, sodium carbomethylcellulose and/or polyvinylpyrrolidone, and, if desired, disintegrators, e.g. starches, agar, alginic acid or a salt thereof, such as sodium alginate, and/or e.g. effervescent mixtures, adsorbents, colourings, flavourings or sweeteners.

For parenteral admininistration there are suitable especially infusion solutions, preferably isotonic aqueous solutions or suspensions, it being possible to prepare these before use, e.g. from lyophilised preparations that contain the active ingredient alone or together with a carrier, e.g. mannitol. Such preparations may be sterilised and/or contain adjuncts, for example preservatives, stabilisers, wetting agents and/or emulsifiers, solubilisers, salts for regulating the osmotic pressure and/or buffers.

For topical and transdermal administration preferably hydrogels, emulsions, such as creams and ointments, and microemulsions such as isotropic transparent emulsion gels are used. Such preparations contain the active ingredient together with e.g. preservatives, stabilizers, thickening agents, emulsifiers, oils, solubilizers and penetration enhancers.

The present pharmaceutical preparations, which, if desied, may contain other pharmacologically active substances, are manufactured in a manner known per se, e.g. by means of conventional mixing, granulating, tabletting, film coating, dissolving, confectioning or lyophilising processes, and contain from approximately 0.1 to 100%, especially from approximately 1 to approximately 50% or, in the case of lyophilisates, up to 100%, of the active ingredient.

Depending upon the type of disorder, the individual condition of the organism and the mode of administration, the daily dose to be administered for the treatment of a warm-blooded animal (human or animal) weighing approximately 70 kg is from approximately 0.05 g to approximately 4 g.

The following Examples (a) to (f) are intended to illustrate the manufacture of some typical forms of administration, but do not in any way represent the only embodiments of those forms of administration.

(a) 250 g of active substance are mixed with 550 g of lactose, 100 g of microcrystalline cellulose and 100 g of maize starch, and the mixture is moistened with an aqueous paste of 100 g maize starch, and granulated by being passed through a sieve. After drying, 60 g of talc, 10 g of magnesium stearate and 20 g of colloidal silica are added and the mixture is pressed to form 10,000 tablets each weighing 119 mg and each containing 25 mg of active substance, which may, if desired, be provided with dividing notches for a finer adjustment of the dosage.

(b) A granulate is prepared from 100 g of active substance, 600 g of lactose, 300 g of cellulose, 200 g of maize starch and an aqueous paste of 120 g of maize starch. After drying, it is mixed with 30 g of colloidal silica, 90 g of talc and 15 g of magnesium stearate and processed so as to form 10,000 film coating cores. These are subsequently coated with an aqueous suspension of 20 g low substituted hydroxypropylmethylcellulose, 15 g of talc and 10 g of titanium dioxide and dried. The resulting film coated tablets each weigh 150 mg and contain 10 mg of active substance.

(c) A sterile solution of 5.0 g of the active substance in 5000 ml of distilled water is introduced into 5 ml ampoules, the ampoules containing 5 mg of active ingredient in 5 ml of solution.

(d) 25 g of active substance and 1975 g of finely ground suppository base (for example, cocoa butter) are thoroughly mixed and then melted. 1000 suppositories of 2 g are cast from the melt which has been kept homogenous by stirring. They each contain 25 mg of active substance.

(e) 25 g of active substance and 120 g of granular lactose, e.g. Tablettose ®, 95 g of microcrystalline cellulose, e.g. Avicel ® PH-102, 7 g of colloidal silicagel and 3 g of magnesium stearate are intimately mixed. The resulting powder is then sieved and filled in 250 mg portions into 1,000 gelatine capsules.

(f) 400 g of active substance are dispersed in 24 l of distilled water with the addition of 70 g of a preservative, e.g. methylparaben, and 530 g of a thickening agent, e.g. carbomer 940, and the corresponding amount of 1N sodium hydroxide solution. 6000 g of petrolatum are mixed with 6000 g of a fatty alcohol, e.g. stearyl alcohol, with the addition of 3000 g of an emulsifier, e.g polyoxyethylene sorbitan monolaurate. Both oil and water phase are heated separately to 70° C. and then mixed together. After homogenisation and cooling, 1000 tubes are filled with 40 g of O/W ointment each.

The following examples are intended to illustrate the invention and are not to be construed as being limitations thereon. Temperatures are given in degrees Centigrade. In examples 1–7, the preparation of o-hydroxyphenyl-benzyl-ketone starting materials of the formula VI is described. Examples 8–17 show the preparation of isoflavone intermediates of the formula IIa. In examples 18–35, the preparation of isoflavans of the formula I is described. Examples 36–71 show the preparation of isoflavans of the formula I including the respective starting materials and intermediates.

EXAMPLE 1

1,2,4-Trihydroxybenzene (40.3 g) is suspended in dry diethylether (250 ml) containing dry $ZnCl_2$ (38.2 g) and 4-methylphenylacetonitrile (49.8 g). The suspension is then exposed for 6 h at 0° to a gentle stream of dry HCl, te gas bubbling through the suspension under continuous stirring. Then the reaction mixture is kept for 50 h at 4° and thereafter the supernatant is decanted from heavy oil which is separated. The oil is washed twice with diethylether, then with water (1 l), and conc. HCl (20 ml) are added and the mixture is boiled for 1 h under reflux. After cooling to room temperature, the mixture is extracted with diethylether (3×250 ml). The combined ether solutions are extracted with NaOH 2N solutions (3×100 ml). The alkali extract is acidified with conc. HCl and the mixture cooled on ice. The crude product is filtered off and recrystallized from methanol/water. The product is dried in vacuo to constant weight to yield 2,4,5-trihydroxyphenyl-4'-methylbenzylketone, m.p. 173°.

EXAMPLE 2

As example 1, but using pyrogallol (39.1 g) instead of 1,2,4-trihydroxybenzene, 52.5 g of 4-methylphenylacetonitrile and 41.0 g of $ZnCl_2$. The suspension is exposed for 10 h at 0° to a stream of HCl. 2,3,4-Trihydroxyphenyl-4'-methylbenzylketone is obtained, m.p. 148°.

EXAMPLE 3

As example 1, but using 2,6-dihydroxytoluene (24.8 g) instead of 1,2,4-trihydroxybenzene, 27.5 g of methylphenylacetonitrile and $AlCl_3$ (26.7 g) instead of $ZnCl_2$. The suspension is exposed for 16 h at 0° to a stream of HCl. After cooling the reaction mixture to room temperature, it is extracted with chloroform instead of diethylether. After evaporating the chloroform extract to a small volume, the crystals of the product are obtained. After drying 2,4-dihydroxy-3-methylphenyl-4'-methylbenzylketone is obtained; m.p. 154°.

EXAMPLE 4

As example 1, but using 2,6-dihydroxytoluene (49.6 g) instead of 1,2,4-trihydroxybenzene, 3,4-dimethoxyphenylacetonitrile (70.9 g) instead of 4-methyphenylacetonitrile and 47.7 g of $ZnCl_2$. The suspension is exposed for 6 h at 0° to a stream of HCl. 2,4-Dihydroxy-3-methylphenyl-3',4'-dimethoxybenzylketone is obtained; m.p. 168°–170°.

EXAMPLE 5

As example 1, but using 2,6-dihydroxytoluene (44.7 g) instead of 1,2,4-trihydroxybenzene, 4-chlorophenylacetonitrile (54.6 g) instead of 4-methylphenylacetonitrile and 47.7 g of $ZnCl_2$. The suspension is exposed for 12 h at 0° to a stream of HCl. 2,4-Dihydroxy-3-methylphenyl-4'-chlorobenzylketone is obtained; m.p. 167°.

EXAMPLE 6

As example 1, but using 45.4 g of 1,2,4-trihydroxybenzene, 4-chlorophenylacetonitrile (56.1 g) instead of 4-methylphenylacetonitrile and $AlCl_3$ (44.7 g) instead of $ZnCl_2$. The suspension is exposed for 12 h at 0° to a stream of HCl. The crude substance is purified by column chromatography (silica gel; chloroform). 2,4,5-Trihydroxyphenyl-4'-chlorobenzylketone is obtained; m.p. 170°.

EXAMPLE 7

As example 1, but using 2,6-dihydroxytoluene (14.9 g) instead of 1,2,4-trihydroxybenzene, 4-nitrophenylacetonitrile (19.5 g) instead of 4-methylphenylacetonitrile and $AlCl_3$ (13.3 g) instead of $ZnCl_2$. The suspension is exposed for 12 h at 0° to a stream of HCl. 2,4-Dihydroxy-3-methylphenyl-4'-nitrobenzylketone is obtained; m.p. 190°–192°.

EXAMPLE 8

2,4,5-Trihydroxyphenyl-4'-methylbenzylketone (3.9 g) is dissolved in dry dimethylformamide (50 ml). To this solution is added dropwise borontrifluoride-diethyletherate (7.4 g); the reaction is exothermic. After adjusting the temperature to 50°, a solution of methanesulfonylchloride (5.2 g) in dry dimethylformamide (25 ml) is added dropwise. This mixture is heated at 90°–100° for 2 h, cooled to room temperature and poured into water (500 ml) while stirring. The separated product is filtered off, washed with water and recrystallized from methanol. The product is dried in vacuo to constant weight to yield 6,7-dihydroxy-3-(4-methylphenyl)-4H-1-benzopyran-4-one; m.p. 280°.

EXAMPLE 9

As example 8, but using 2,3,4-trihydroxypheyl-4'-methylbenzylketone instead of 2,4,5-trihydroxyphenyl-4'-methylbenzylketone. 7,8-Dihydroxy-3-(4-methylphenyl)-4H-1-benzopyran-4-one is obtained; m.p. 225°.

EXAMPLE 10

As example 8, but using 2,4-dihydroxy-3-methylphenyl-4'-methylbenzylketone instead of 2,4,5-trihydroxyphenhl-4'-methylbenzylketone. 7-Hydroxy-8-methyl-3-(4-methylphenyl)-4H-1-benzopyran-4-one is obtained; m.p. 264°–267°.

EXAMPLE 11

As example 8, but using 2,4-dihydroxy-3-methylphenyl-4'-methoxybenzylketone [J. Indian Chem. Soc. 39, 301 (1962)] instead of 2,4,5-trihydroxyphenyl-4'-methylbenzylketone. 7-Hydroxy-8-methyl-3-(4-methoxyphenyl)-4H-1-benzopyran-4-one is obtained; m.p. 235°.

EXAMPLE 12

As example 8, but using 2,4-dihydroxy-3-methylphenyl-3',4'-dimethoxybenzylketone instead of 2,4,5-trihydroxyphenyl-4'-methylbenzylketone. 7-Hydroxy-8-methyl-3-(3,4-dimethoxyphenyl)-4H-1-benzopyran-4-one is obtained; m.p. 234°.

EXAMPLE 13

As example 8, but using 2,4-dihydroxy-3-methylphenyl-4'-chlorobenzylketone instead of 2,4,5-trihydroxyphenyl-4'-methylbenzylketone. 7-Hydroxy-8-methyl-3-(4-chlorophenyl)-4H-1-benzopyran-4-one is obtained; m.p. 275°.

EXAMPLE 14

As example 8, but using 2,4,5-trihydroxyphenyl-4'-chlorobenzylketone instead of 2,4,5-trihydroxyphenyl-4'-methylbenzylketone. 6,7-Dihydroxy-3-(4-chlorophenyl)-4H-1-benzopyran-4-one is obtained; m.p. 299°.

EXAMPLE 15

As example 8, but using 2,4-dihydroxy-3-methylphenyl-4'-nitrobenzylketone instead of 2,4,5-trihydroxyphenyl-4'-methylbenzylketone. 7-Hydroxy-8-methyl-3-(4-nitrophenyl)-4H-1-benzopyran-4-one is obtained; m.p. 345°.

EXAMPLE 16

7-Hydroxy-8-methyl-3-(3,4-dimethoxyphenyl)-4H-1-benzoyran-4-one [see example 12] (3.12 g) is dissolved in dimethylformamide (15 ml) and $K_2CO_3$ (3.5 g) is added to the solution. While stirring, epibromhydrine (2.47 g) is dropped into the mixture. After heating for 5 h at 60°, the content of the reaction flask is poured into water (500 ml) and the precipitated product is filtered off and recrystallized from ethanol. The product is dried in vacuo to constant weight to yield 7-(2,3-epoxypropoxy)-8-methyl-3-(3,4-dimethoxyphenyl)-4H-1-benzopyran-4-one, m.p. 214°.

EXAMPLE 17

6,7-Methylenedioxy-3-(4-hydroxyphenyl)-4H-1-benzopyran-4-one [cp. Nippon Kagaku Zasshi 85, 793 (1964), Agr. Biol. Chem. (Tokyo) 32, 740 (1968) and Angew. Chem. 93, 129 (1981)] (2.0 g) is dissolved in dimethylformamide (15 ml) and $K_2CO_3$ (2.8 g) is added to the solution. While stirring, 2-bromoethylbutyrate (2.7 g) is dropped into the mixture. The content of the reaction flask is refluxed for 30 min. After cooling, water (50 ml) is added and the mixture is extracted with chloroform (3×30 ml), the extract washed with water (3×15 ml) and dried over $Na_2SO_4$. Chloroform is removed under reduced pressure and the residue is recrystallized from methanol. The product is dried in vacuo to constant weight to yield 6,7-methylenedioxy-3-[4-(1-ethoxycarbonyl-1-propyloxy)-phenyl]-4H-1-benzopyran-4-one, m.p. 119°–121°.

EXAMPLE 18

6,7-Dihydroxy-3-(3,4-dimethoxyphenyl)-4H-1-benzopyran-4-one [Indian J. Chem. Sect. B 19B, 82 (1980) and Indian J. Chem. Sect. B 15B, 1049 (1977)] (25 g) in a mixture of dioxane and ethanol 1:1 (1250 ml) is hydrogenated for 8 days at normal pressure and room temperature over palladium 10% on active charcoal (2.5 g) in the presence of concentrated $H_2SO_4$ (2.5 ml). After filtration of the catalyst, the filtrate is evaporated under reduced pressure to a volume of about 50 ml and diluted with water till turbidity appears. After cooling the solution, a solid precipitates. It is filtered off and recrystallized from ethanol. The product is dried in vacuo to constant weight to yield 3,4-dihydro-6,7-dihydroxy-3-(3,4-dimethoxyphenyl)-2H-1-benzopyran, m.p. 153°.

EXAMPLE 19

As example 18, with the same proportions of chemicals, but using 6,7-dihydroxy-3-(4-methylphenyl)-4H-1-benzopyran-4-one (16 g) instead of 6,7-dihydroxy-3-(3,4-dimethoxyphenyl)-4H-1-benzopyran-4-one.

The substance is hydrogenated for 24 h. 3,4-Dihydro-6,7-dihydroxy-3-(4-methlphenyl)-2H-1-benzopyran is obtained; m.p. 166°.

EXAMPLE 20

As example 18, with the same proportions of chemicals, but using 6,7-methylenedioxy-3-(4-methoxyphenyl)-4H-1-benzopyran-4-one [Nippon Kagaku Zasshi 85, 793 (1964)] (17 g) instead of 6,7-dihydroxy-3-(3,4-dimethoxyphenyl)-4H-1-benzopyran-4-one. The substance is hydrogenated for 2 days. 3,4-Dihydro-6,7-methylenedioxy-3-(4-methoxyphenyl)-2-1-benzopyran is obtained; m.p. 131°.

EXAMPLE 21

As example 18, with the same proportions of chemicals, but using 7,8-dihydroxy-3-(4-methoxyphenyl)-4H-1-benzopyran-4-one [J. Sci. Ind. Research (India) 20B, 334 (1961)](5 g) instead of 6,7-dihydroxy-3-(3,4-dimethoxyphenyl)-4H-1-benzopyran-4-one. The substance is hydrogenated for 7 days. 3,4-Dihydro-7,8-dihydroxy-3-(4-methoxypheny)-2-1-benzopyran is obtained; m.p. 156°.

EXAMPLE 22

As example 18, with the same proportions of chemicals, but using 7,8-dihydroxy-3-(3,4-dimethoxyphenyl)-4H-1-benzopyran-4-one [Tetrahedron 18, 1443 (1962)] (10 g) instead of 6,7-dihydroxy-3-(3,4-dimethoxyphenyl)-4H-1-benzopyran-4-one. The substance is hydrogenated for 7 days. 3,4-Dihydro-7,8-dihydroxy-3-(3,4-dimethoxyphenyl)-2H-1-benzopyran is obtained; m.p. 176°.

EXAMPLE 23

As example 18, with the same proportions of chemicals, but using 7,8-dihydroxy-3-(4-methylphenyl)-4H-1-benzopyran-4-one (1.9 g) instead of 6,7-dihydroxy-3-(3,4-dimethoxyphenyl)-4H-1-benzopyran-4-one. The substance is hydrogenated for 23 h. 3,4-Dihydro-7,8-dihydroxy-3-(4-methylphenyl)-2H-1-benzopyran is obtained; m.p. 164°.

EXAMPLE 24

As example 18, with the same proportions of chemicals, but using 7-hydroxy-8-methyl-3-(3,4-dimethoxyphenyl)-4H-1-benzopyran-4-one (10 g) instead of 6,7-dihydroxy-3-(3,4-dimethoxyphenyl)-4H-1-benzopyran-4-one. The substance is hydrogenated for 10 days. 3,4-Dihydro-7-hydroxy-8-methyl-3-(3,4-dimethoxyphenyl)-2H-1-benzopyran is obtained; m.p. 125°-127°.

EXAMPLE 25

As example 18, with the same proportions of chemicals, but using 7-hydroxy-8-methyl-3-(4-chlorophenyl)-4H-1-benzopyran-4-one (5 g) instead of 6,7-dihydroxy-3-(3,4-dimethoxyphenyl)-4H-1-benzopyran-4-one. The substance is hydrogenated for 5 days. 3,4-Dihydro-7-hydroxy-8-methyl-3-(4-chlorophenyl)-2H-1-benzopyran is obtained; m.p. 159°.

EXAMPLE 26

7-Hydroxy-8-methyl-3-(4-methylphenyl)-4H-1-benzopyran-4-one (400 mg) in a mixture of dioxane and ethanol 1:1 (200 ml) is hydrogenated for 64 h at room temperature over palladium 10% on active charcoal (100 mg) in the presence of p-toluenesulfonic acid monohydrate (120 mg). After filtration of the catalyst, the filtrate is evaporated under reduced pressure to a volume of about 50 ml. Water (150 ml) is added and the solution is extracted with dichloromethane (3×100 ml). The combined organic solutions are washed with water, dried and evaporated. The product is dried in vacuo to constant weight to yield 3,4-dihydro-7-hydroxy-8-methyl-3-(4-methylphenyl)-2H-1-benzopyran, m.p. 136°-137°.

EXAMPLE 27

As example 26, but using 7,8-dihydroxy-3-(4-hydroxyphenyl)-4H-1-benzopyran-4-one [J. Sci. Ind. Research (India) 20B, 334 (1961)] (540 mg) instead of 7-hydroxy-8-methyl-3-(4-methylphenyl)-4H-1-benzopyran-4-one. A crystalline precipitate is formed when water is added; it is filtrated off and washed with water. 3,4-Dihydro-7,8-dihydroxy-3-(4-hydroxyphenyl)-2H-1-benzopyran is obtained; m.p. 225°-226°.

EXAMPLE 28

As example 26, but using 7-hydroxy-8-methyl-3-(4-methoxyphenyl)-4H-1-benzopyran-4-one (28 mg) instead of 7-hydroxy-8-methyl-3-(4-methylphenyl)-4H-1-benzopyran-4-one. A crystalline precipitate is formed when water is added; it is filtrated off and washed with water. 3,4-Dihydro-7-hydroxy-8-methyl-3-(4-methoxyphenyl)-2H-1-benzopyran is obtained; m.p. 140°-141°.

EXAMPLE 29

As example 26, but using 6,7-methylenedioxy-3-[4-(1-ethoxycarbonyl-1-propyloxy)-phenyl]-4H-1-benzopyran-4-one (25 mg) instead of 7-hydroxy-8-methyl-3-(4-methylphenyl)-4H-1-benzopyran-4-one. After filtration of the catalyst, the solvent is evaporated and the residue is purified by column chromatography on silica gel using dichloromethane as eluant. 3,4-Dihydro-6,7-methylenedioxy-3-[4-(1-ethoxycarbonyl-1-propyloxy)-phenyl]-2H-1-benzopyran is obtained as an oil; $^1$H-NMR ($d_6$-DMSO): $\delta$=6.9, 7.0, 7.4 (d), 7.6 (d) [6H, Aromaten-H]; 3,4 (m, 2H, $CH_2$); 2.5 (m, 2H, $CH_2$); 1.8 (t, 3H, $CH_3$); 1.6 (t, 3H, $CH_3$). MS: m/e=384 ($M^+$).

EXAMPLE 30

7-Hydroxy-8-methyl-3-(4-nitrophenyl)-4H-1-benzopyran-4-one (440 mg), dissolved in a mixture of dioxane/ethanol 1:1 (200 ml), is hydrogenated for 15 h at room temperatutre over Raney nickel (200 mg). After filtration of the catalyst, the filtrate is evaporated under reduced pressure. The residue is dissolved in ethanol (75 ml) and hydrogenated for 15 h at room temperature over palladium 10% on active charcoal (200 mg) in the presence of p-toluenesulfonic acid monohydrate (760 mg). After filtration of the catalyst, the filtrate is evaporated under reduced pressure. The residue is dissolved in water (100 ml). The solution is neutralized to pH 7.5 by addition of a saturated solution of $NaHCO_3$ and extracted with ethyl acetate (3×50 ml). The combined organic solutions are washed with water (2×20 ml), dried over $MgSO_4$ and evaporated. The residue is purified by column chromatography on silica gel using dichloromethane/ethyl acetate 1:1 as eluent. The product is dried in vacuo to constant weight to yield 3,4-dihydro-7-hydroxy-8-methyl-3-(4-aminophenyl)-2H-1-benzopyran, m.p. 150°–151°.

EXAMPLE 31

3,4-Dihydro-6,7-dihydroxy-3-(4-methoxyphenyl)-2H-1-benzopyran [cp. U.S. Pat. No. 4,264,509] (10.0 g) is dissolved in dry pyridine (30 ml) and acetic anhydride (30 ml) is added. The solution is kept at room temperature for 48 h. Pyridine and the excess of the reagent are removed by evaporating with ethanol under reduced pressure. The residue is purified by column chromatography on silica gel using chloroform as eluent. The crude product is recrystallized from methanol. The product is dried in vacuo to constant weight to yield 3,4-dihydro-6,7-diacetoxy-3-(4-methoxyphenyl)-2H-1-benzopyran, m.p. 104°.

EXAMPLE 32

As example 31, but using 3,4-dihydro-6,7-dihydroxy-3-(4-hydroxyphenyl)-2H-1-benzopyran [cp. Phytochemistry 23, 2203 (1984) and U.S. Pat. No. 4,264,509] (10.3 g) instead of 3,4-dihydro-6,7-dihydroxy-3-(4-methoxyphenyl)-2H-1-benzopyran. 3,4-Dihydro-6,7-diacetoxy-3-(4-acetoxyphenyl)-2H-1-benzopyran is obtained; m.p. 145°–147°.

EXAMPLE 33

As example 31, but using 3,4-dihydro-6,7-dihydroxy-3-phenyl-2H-1-benzopyran [cp. U.S. Pat. No. 4,264,509] (9.7 g) instead of 3,4-dihydro-6,7-dihydroxy-3-(4-methoxyphenyl)-2H-1-benzopyran. 3,4-Dihydro-6,7-diacetoxy-3-phenyl-2H-1-benzopyran is obtained; m.p. 102°.

EXAMPLE 34

Triethylamine (4.0 g) and dichlorodiphenylmethane (3.5 g) are added to a solution of 3,4-dihydro-6,7-dihydroxy-3-(4-methoxyphenyl)-2H-1-benzopyran [cp. U.S. Pat. No. 4,264,509] (1.4 g) in pyridine (50 ml) containing 1% of water. The solution is warmed at 50° for 6 h and then poured into a mixture of water and 5N HCl 2:1 (150 ml). It is extracted with dichloromethane (3×50 ml) and the combined organic solutions are washed with water. The solvent is evaporated to dryness under reduced pressure. The residue is recrystallized from ethanol. After drying in vacuo to constant weight, 3,4-dihydro-6,7-diphenylmethylenedioxy-3-(4-methoxyphenyl)-2H-1-benzopyran is obtained; m.p. 138°–139°.

EXAMPLE 35

Triethylamine (2.02 g) and 3,4-dihydro-7,8-dihydroxy-3-(3,4-dimethoxyphenyl)-2H-1-benzopyran [see example 22] (0.75 g) are dissolved in pyridine (20 ml) containing 1% of water. A solution of dichlorodiphenylmethane (1.77 g) in pyridine (5 ml) is slowly added. The mixture is heated at 70° for 4 h. The solution is then poured into water (250 ml) and evaporated invacuo to a volume of about 100 ml. It is then extracted with ethyl acetate (3×100 ml), the combined organic solutions are washed with water (2×50 ml) and evaporated to dryness under reduced pressure. The residue is purified by column chromatography on silica gel using dichloromethane/hexane 1:1 as eluent. The product is recrystallized from hexane. After drying in vacuo to constant weight, 3,4-dihydro-7,8-diphenylmethylenedioxy-3-(3,4-dimethoxyphenyl)-2H-1-benzopyran is obtained; m.p. 137°–138°.

EXAMPLE 36

7,8-Dihydroxy-3-(3-methylphenyl)-4H-1-benzopyran-4-one (100 mg), dissolved in a mixture of ethanol/dioxan 2:1 (75 ml), is hydrogenated for 24 h at room temperature over palladium 10% on active charcoal (50 mg) in the presence of p-toluenesulphonic acid monohydrate (50 mg). After filtration of the catalyst, the filtrate is evaporated under vacuum to a minimum volume, then diluted with water (75 ml) and neutralized to pH 7 by addition of a saturated solution of $NaHCO_3$. An oil is obtained which is extracted with ethyl acetate. The extract is dried over magnesium sulphate and evaporated under vacuum to yield an amorphous solid which is dissolved in methylene chloride and eluted on a silica gel column. After evaporation of the main fraction, one obtains 3,4-dihydro-7,8-dihydroxy-3-(3-methylphenyl)-2H-1-benzopyran, m.p. 95°–96°.

The starting materials are prepared as follows:

(a) As example 8, but using 2,3,4-trihydroxyphenyl-3'-methylbenzylketone instead of 2,4,5-trihydroxyphenyl-4'-methylbenzylketone. 7,8-Dihydroxy-3-(3-methylphenyl)-4H-1-benzopyran-4-one is obtained, m.p. 268°.

(b) As example 1, but using pyrogallol instead of 1,2,4-trihydroxybenzene and 3-methylphenylacetonitrile instead of 4-methylphenylacetonitrile. 2,3,4-Trihydroxyphenyl-3'-methylbenzylketone is obtained, m.p. 141°.

EXAMPLE 37

As example 36, but using 7,8-dihydroxy-3-(3-carboxyphenyl)-4H-1-benzopyran-4-one (100 mg) instead of 7,8-dihydroxy-3-(3-methylphenyl)-4H-1-benzopyran-4-one. After neutralization to pH 7 by addition of a saturated solution of $NaHCO_3$, there is a precipitation of crystals of 3,4-dihydro-7,8-dihydroxy-3-(3-carboxyphenyl)-2H-1-benzopyran, m.p. 194°–195°.

The starting materials are prepared as follows:

(a) As example 8, but using 2,3,4-trihydroxyphenyl-3'-carboxybenzylketone instead of 2,4,5-trihydroxyphenyl-4'-methylbenzylketone. 7,8-Dihydroxy-3-(3-carboxyphenyl)-4H-1-benzopyran-4-one is obtained, m.p. 313°–314°.

(b) As example 1, but using pyrogallol instead of 1,2,4-trihydroxybenzene and 3-carboxyphenylacetonitrile instead of 4-methylphenylacetonitrile. 2,3,4-Trihydroxyphenyl-3'-carboxybenzylketone is obtained, m.p. 222°.

EXAMPLE 38

As example 36, but using 7,8-dihydroxy-3-(4-nitrophenyl)-4H-1-benzopyran-4-one [cp. J. Sci. Ind. Research (India) 20B, 334 (1961)] (300 mg) instead of 7,8-dihydroxy-3-(3-methylphenyl)-4H-1-benzopyran-4-one. After neutralization to pH 7 by addition of a saturated solution of $NaHCO_3$, a precipitate is obtained which is filtered, washed with water and dried under vacuum over phosphorous pentoxide. The mother liquor is acidified to pH 4.5 and extracted with ethyl acetate. The organic layer is evaporated to dryness under vacuum to yield a solid. The two fractions consist of 3,4-dihydro-7,8-dihydroxy-3-(4-aminophenyl)-2H-1-benzopyran, m.p. 210°–212°.

EXAMPLE 39

6,7-Dihydroxy-3-(3-methylphenyl)-4H-1-benzopyran-4-one (1.2 g), dissolved in a mixture of dioxan/ethanol 4:6 (40 ml), is hydrogenated for 24 h at room temperature over palladium 5% on active charcoal (0.48 g) in the presence of a few drops of concentrated sulphuric acid. After filtration of the catalyst, the filtrate is evaporated to dryness under vacuum. An oil is obtained which is dissolved in methylene chloride. The solution is washed with water and dried over magnesium sulphate to give an oil which on crystallization yields 3,4-dihydro-6,7-dihydroxy-3-(3-methylphenyl)-2H-1-benzopyran, m.p. 146°–148°.

The starting materials are prepared as follows:

(a) As example 8, but using 2,4,5-trihydroxyphenyl-3'-methylbenzylketone instead of 2,4,5-trihydroxyphenyl-4'-methylbenzylketone. 6,7-Dihydroxy-3-(3-methylphenyl)-4H-1-benzopyran-4-one is obtained, m.p. 258°.

(b) As example 1, but using 3-methylphenylacetonitrile instead of 4-methylphenylacetonitrile. 2,4,5-Trihydroxyphenyl-3'-methylbenzylketone is obtained, m.p. 197°.

EXAMPLE 40

6,7-Dihydroxy-3-(4-fluorophenyl)-4H-1-benzopyran-4-one (1.2 g), dissolved in a mixture of dioxan/ethanol 4:6 (40 ml), is hydrogenated for 24 h at room temperature over palladium 5% on active charcoal (0.48 g) in the presence of a few drops of conc. sulphuric acid. After filtration of the catalyst, the filtrate is evaporated to dryness under vacuum. An oil is obtained which crystallizes to give 3,4-dihydro-6,7-dihydroxy-3-(4-fluorophenyl)-2H-1-benzopyran, m.p. 135°–137°.

The starting materials are prepared as follows:

(a) As example 8, but using 2,4,5-trihydroxyphenyl-4'-fluorobenzylketone instead of 2,4,5-trihydroxyphenyl-4'-methylbenzylketone. 6,7-Dihydroxy-3-(4-fluorophenyl)-4H-1-benzopyran-4-one is obtained, m.p. 296°.

(b) As example 1, but using 4-fluorophenylacetonitrile instead of 4-methylphenylacetonitrile. 2,4,5-Trihydroxyphenyl-4'-fluorobenzylketone is obtained, m.p. 189°–190°.

EXAMPLE 41

As example 40, but using 7,8-dihydroxy-3-phenyl-4H-1-benzopyran-4-one [cp. Zh. Org. Khim. 40, 2459 (1970) and Zh. Org. Khim. 5, 515 (1969)] (1.2 g) instead of 6,7-dihydroxy-3-(4-fluorophenyl)-4H-1-benzopyran-4-one. After evaporation of the filtrate, the residue is washed with water and dried under vacuum to give 3,4-dihydro-7,8-dihydroxy-3-phenyl-2H-1-benzopyran, m.p. 138°.

EXAMPLE 42

As example 36, but using 6,7-dihydroxy-3-(3,4-methylenedioxyphenyl)-4H-1-benzopyran-4-one [cp. Bull. Chem. Soc. Japan 38, 612 (1965)] (900 mg) instead of 7,8-dihydroxy-3-(3-methylphenyl)-4H-1-benzopyran-4-one. After neutralization to pH 7, a precipitate is obtained which is purified by elution on a silica gel column (CHCl₃/diisopropylether 1:1) to yield 3,4-dihydro-6,7-dihydroxy-3-(3,4-methylenedioxyphenyl)-2H-1-benzopyran, m.p. 163°–164°.

EXAMPLE 43

As example 40, but using 6-n-hexyl-7-hydroxy-3-(4-methoxyphenyl)-4H-1-benzopyran-4-one (1.2 g) instead of 6,7-dihydroxy-3-(4-fluorophenyl)-4H-1-benzopyran-4-one. After evaporation of the filtrate, the residue is eluted on a silicagel column (CH₂Cl₂): the main fraction yields an oil which crystallizes and represents 3,4-dihydro-6-n-hexyl-7-hydroxy-3-(4-methoxyphenyl)-2H-1-benzopyran, m.p. 64°–66°.

The starting materials are prepared as follows:

(a) As example 8, but using 5-n-hexyl-2,4-dihydroxyphenyl-4'-methoxybenzylketone instead of 2,4,5-trihydroxyphenyl-4'-methylbenzylketone. 6-n-Hexyl-7-hydroxy-3-(4-methoxyphenyl)-4H-1-benzopyran-4-one is obtained, m.p. 188°.

(b) As example 1, but using 4-n-hexylresorcinol instead of 1,2,4-trihydroxybenzene and 4-methoxyphenylacetonitrile instead of 4-methylphenylacetonitrile. 5-n-Hexyl-2,4-dihydroxyphenyl-4'-methoxybenzylketone is obtained, m.p. 137°.

EXAMPLE 44

As example 36, but using 7,8-dihydroxy-3-(3-fluorophenyl)-4H-1-benzopyran-4-one (544 mg) instead of 7,8-dihydroxy-3-(3-methylphenyl)-4H-1-benzopyran-4-one. After extraction with ethyl acetate, the organic solution is washed with water and evaporated under vacuum to yield 3,4-dihydro-7,8-dihydroxy-3-(3-fluorophenyl)-2H-1-benzopyran, m.p. 148°–149°.

The starting materials are prepared as follows:

(a) As example 8, but using 2,3,4-trihydroxyphenyl-3'-fluorobenzylketone instead of 2,4,5-trihydroxyphenyl-4'-methylbenzylketone. 7,8-Dihydroxy-3-(3-fluorophenyl)-4H-1-benzopyran-4-one is obtained, m.p. 230°.

(b) As example 1, but using pyrogallol instead of 1,2,4-trihydroxybenzene and 3-fluorophenylacetonitrile instead of 4-methylphenylacetonitrile. 2,3,4-Trihydroxyphenyl-3'-fluorobenzylketone is obtained, m.p. 162.

EXAMPLE 45

As example 40, but using 6,7-dihydroxy-3-(3-fluorophenyl)-4H-1-benzopyran-4-one (1.2 g) instead of 6,7-dihydroxy-3-(4-fluorophenyl)-4H-1-benzopyran-4-one. After evaporation of the filtrate, the oily residue is dissolved in methylene chloride. The solution is washed with water, dried over magnesium sulphate and evaporated to dryness under vacuum. The residue is purified by elution on a silica gel column (CHCl₃/diisopropyl ether 1:1) and the oil representing the main fraction on crystallization yields 3,4-dihydro-6,7-dihydroxy-3-(3-fluorophenyl)-2H-1-benzopyran, m.p. 121°–123°.

The starting materials are prepared as follows:

(a) As example 8, but using 2,4,5-trihydroxyphenyl-3'-fluorobenzylketone instead of 2,4,5-trihydroxyphenyl-4'-methylbenzylketone. 6,7-Dihydroxy-3-(3-fluorophenyl)-4H-1-benzopyran-4-one is obtained, m.p. 277°.

(b) As example 1, but using 3-fluorophenylacetonitrile instead of 4-methylphenylacetonitrile. 2,4,5-Trihydroxyphenyl-3'-fluorobenzylketone is obtained, m.p. 209°.

EXAMPLE 46

As example 36, but using 7-hydroxy-8-methyl-3-(3,4-methylenedioxyphenyl)-4H-1-benzopyran-4-one (100 mg) instead of 7,8-dihydroxy-3-(3-methylphenyl)-4H-1-benzopyran-4-one. After neutralization to pH 7, a precipitate is formed which is filtered, washed with water and dried under vacuum to give 3,4-dihydro-7-hydroxy-8-methyl-3-(3,4-methylenedioxyphenyl)-2H-1-benzopyran, m.p. 130°–131°.

The starting materials are prepared as follows:

(a) As example 8, but using 2,4-dihydroxy-3-methylphenyl-3',4'-methylenedioxybenzylketone instead of 2,4,5-trihydroxyphenyl-4'-methylbenzylketone. 7-Hydroxy-8-methyl-3-(3,4-methylenedioxyphenyl)-4H-1-benzopyran-4-one is obtained, m.p. 270°–272°.

(b) As example 1, but using 2,6-dihydroxytoluene instead of 1,2,4-trihydroxybenzene and 3,4-methylenedioxyphenylacetonitrile instead of 4-methylphenylacetonitrile. 2,4-Dihydroxy-3-methylphenyl-3',4'-methylenedioxybenzylketone is obtained, m.p. 164°.

EXAMPLE 47

As example 36, but using 7-hydroxy-8-methyl-3-(3-ethoxycarbonylphenyl)-4H-1-benzopyran-4-one (100 mg) instead of 7,8-dihydroxy-3-(3-methylphenyl)-4H-1-benzopyran-4-one. After neutralization, a crystalline precipitate is formed which is filtered, washed with water and dried under vacuum to give 3,4-dihydro-7-hydroxy-8-methyl-3-(3-ethoxycarbonylphenyl)-2H-1-benzopyran, m.p. 143°–144°.

The starting materials are prepared as follows:

(a) As example 8, but using 2,4-dihydroxy-3-methylphenyl-3'-ethoxycarbonylbenzylketone instead of 2,4,5-trihydroxyphenyl-4'-methylbenzylketone. 7-Hydroxy-8-methyl-3-(3-ethoxycarbonylphenyl)-4H-1-benzopyran-4-one is obtained, m.p. 222°.

(b) As example 1, but using 2,6-dihydroxytoluene instead of 1,2,4-trihydroxybenzene and 3-ethoxycarbonylphenylacetonitrile instead of 4-methylphenylacetonitrile. 2,4-Dihydroxy-3-methylphenyl-3'-ethoxycarbonylbenzylketone is obtained, m.p. 157°.

EXAMPLE 48

As example 36, but using 7-hydroxy-8-methyl-3-trifluoromethylphenyl)-4H-1-benzopyran-4-one (100 mg) instead of 7,8-dihydroxy-3-(3-methylphenyl)-4H-1-benzopyran-4-one. After extraction with ethyl acetate, the organic layer is washed with water, dried over magnesium sulphate, then evaporated under vacuum to give 3,4-dihydro-7-hydroxy-8-methyl-3-(3-trifluoromethylphenyl)-2H-1-benzopyran as an oil. $^1$H-NHR (d$_6$-DMSO): $\delta = 7.6$ (m, 4H, Aromaten-H); 6.7 (d, 1H, Arom.-H); 6.4 (d, 1H, Arom.-H); 2.0 (s, 3H, CH$_3$). MS: m/e = 308 (M+).

The starting materials are prepared as follows:

(a) As example 8, but using 2,4-dihydroxy-3-methylphenyl-3'-trifluoromethylbenzylketone instead of 2,4,5-trihydroxyphenyl-4'-methylbenzylketone. 7-Hydroxy-8-methyl-3-(3-trifluoromethylphenyl)-4H-1-benzopyran-4-one is obtained, m.p. 283°–284°.

(b) As example 1, but using 2,6-dihydroxytoluene instead of 1,2,4-trihydroxybenzene and 3-trifluoromethylphenylacetonitrile instead of 4-methylphenylacetonitrile. 2,4-Dihydroxy-3-methylphenyl-3'-trifluoromethylbenzylketone is obtained, m.p. 167°.

EXAMPLE 49

As example 40, but using 7,8-dimethoxy-3-(4-methylphenyl)-4H-1-benzopyran-4-one (1.2 g) instead of 6,7-dihydroxy-3-(4-fluorophenyl)-4H-1-benzopyran-4-one. After evaporation of the filtrate, the residue is washed with water and dried under vacuum to yield 3,4-dihydro-7,8-dimethoxy-3-(4-methylphenyl)-2H-1-benzopyran, m.p. 98°99°.

The starting material is prepared as follows:

(a) 7,8-Dihydroxy-3-(4-methylphenyl)-4H-1-benzopyran-4-one (2.7 g), described in example 9, is dissolved in dry acetone (50 ml). Pyrolyzed potassium carbonate (4.14 g) is added and the mixture is heated to reflux. A solution of methyl sulphate (3.78 g) in acetone (10 ml) is then added dropwise and heating is maintained for three more hours. After cooling, the solid is filtered and the solution is evaporated to dryness under vacuum. Water is added to the residue which is filtered, washed with an aqueous sodium hydroxide solution (1N) then with water and dried. After crystallization in methanol, 7,8-dimethoxy-3-(4-methylphenyl)-4H-1-benzopyran-4-one is obtained, m.p. 135°.

EXAMPLE 50

As example 39, but using 7-hydroxy-8-methyl-3-(4-chlorophenyl)-4H-1-benzopyran-4-one (1.2 g) instead of 6,7-dihydroxy-3(3-methylphenyl)-4H-1-benzopyran-4-one. Tetrahydrofuran and acetic acid are used instead of dioxan/ethanol and sulphuric acid. The resulting oil is finally purified by elution on a silica gel column (CHCl$_3$) to yield 3,4-dihydro-7-hydroxy-8-methyl-3-(4-chlorophenyl)-2H-1-benzopyran, m.p. 98°–100°.

The starting materials are prepared as follows:

(a) As example 8, but using 2,4-dihydroxy-3-methylphenyl-4'-chlorobenzylketone instead of 2,4,5-trihydroxyphenyl-4'-methylbenzylketone. 7-Hydroxy-8-methyl-3-(4-chlorophenyl)-4H-1-benzopyran-4-one is obtained, m.p. 296°–297°.

(b) As example 1, but using 2,6-dihydroxytoluene instead of 1,2,4-trihydroxybenzene and 4-chlorophenylacetonitrile instead of 4-methylphenylacetonitrile. 2,4-Dihydroxy-3-methylphenyl-4'-chlorobenzylketone is obtained, m.p. 167°.

EXAMPLE 51

As example 39, but using 6,7-dihydroxy-3-(4-aminophenyl)-4H-1-benzopyran-4-one (1.2 g) instead of 6,7-dihydroxy-3-(3-methylphenyl)-4H-1-benzopyran-4-one. The resulting oil corresponds to 3,4-dihydro-6,7-dihydroxy-3-(4-aminophenyl)-2H-1-benzopyran. It is converted to the correspnding hydrochloride and also to the corresponding hemisulfate.

The starting material is prepared as follows:

(a) 6,7-Dihydroxy-3-(4-nitrophenyl)-4H-1-benzopyran-4-one [cp. J. Inst. Chem. (Calcutta) 43, 234 (1971)] (1 g) is dissolved in 250 ml of a mixture of dioxan and ethanol 1:1. Raney nickel (0.45 g) is added and the mixture is hydrogenated for 18 h at room temperature, then filtered. The solution is evaporated under vacuum to about one third of its original volume until a precipitate occurs which is filtered and crystallized in dioxan to give 6,7-dihydroxy-3-(4-aminophenyl)-4H-1-benzopyran-4-one, m.p. 305°–306°.

EXAMPLE 52

As example 39, but using 6,7-dihydroxy-3-(3-chlorophenyl)-4H-1-benzopyran-4-one (1.2 g) instead of 6,7-dihydroxy-3-(3-methylphenyl)-4H-1-benzopyran-4-one. Tetrahydrofuran and acetic acid are used instead of dioxan/ethanol and sulphuric acid. The resulting oil crystallizes to give 3,4-dihydro-6,7-dihydroxy-3-(3-chlorophenyl)-2H-1-benzopyran.

The starting materials are prepared as follows:

(a) As example 8, but using 2,4,5-trihydroxyphenyl-3'-chlorobenzylketone instead of 2,4,5-trihydroxyphenyl-4'-methylbenzylketone. 6,7-Dihydroxy-3-(3-chlorophenyl)-4H-1-benzopyran-4-one is obtained, m.p. 308°.

(b) As example 1, but using 3-chlorophenylacetonitrile instead of 4-methylphenylacetonitrile. 2,4,5-Trihydroxyphenyl-3'-chlorobenzylketone is obtained, m.p. 212°.

EXAMPLE 53

As example 40, but using 6,7-dihydroxy-3-(3-trifluoromethylphenyl)-4H-1-benzopyran-4-one (1.2 g) instead of 6,7-dihydroxy-3-(4-fluorophenyl)-4H-1-benzopyran-4-one. After evaporation of the filtrate, the residue is dissolved in methylene chloride. The solution is washed with water, dried over magnesium sulphate and evaporated under vacuum to yield 3,4-dihydro-6,7-dihydroxy-3-(3-trifluoromethylphenyl)-2H-1-benzopyran, m.p. 139°–141°.

The starting materials are prepared as follows:

(a) As example 8, but using 2,4,5-trihydroxyphenyl-3'-trifluoromethylbenzylketone instead of 2,4,5-trihydroxyphenyl-4'-methylbenzylketone. 6,7-Dihydroxy-3-(3-trifluoromethylphenyl)-4H-1-benzopyran-4-one is obtained, m.p. 274°–275°.

(b) As example 1, but using 3-trifluoromethylphenylacetonitrile instead of 4-methylphenylacetonitrile. 2,4,5-Trihydroxyphenyl-3'-trifluoromethylbenzylketone is obtained, m.p. 170°.

EXAMPLE 54

As example 39, but using 7,8-dihydroxy-3-(3-trifluoromethylphenyl)-4H-1-benzopyran-4-one (1.2 g) instead of 6,7-dihydroxy-3-(3-methylphenyl)-4H-1-benzopyran-4-one. The resulting oil is finally purified by elution on a silica gel column (CH$_2$Cl$_2$) to give 3,4-dihydro-7,8-dihydroxy-3-(3-trifluoromethylphenyl)-2H-1-benzopyran, m.p. 99°–100°.

The starting materials are prepared as follows:

(a) As example 8, but using 2,3,4-trihydroxyphenyl-3'-trifluoromethylbenzylketone instead of 2,4,5-trihydroxyphenyl-4'-methylbenzylketone. 7,8-Dihydroxy-3-(3-trifluoromethylphenyl)-4H-1-benzopyran-4-one is obtained, m.p. 225°.

(b) As example 1, but using pyrogallol instead of 1,2,4-trihydroxybenzene and 3-trifluoromethylphenylacetonitrile instead of 4-methylphenylacetonitrile. 2,3,4-Trihydroxyphenyl-3'-trifluoromethylbenzylketone is obtained, m.p. 171°.

EXAMPLE 55

As example 39, but using 7,8-dihydroxy-3-(3-chlorophenyl)-4H-1-benzopyran-4-one (1.2 g) instead of 6,7-dihydroxy-3-(3-methylphenyl)-4H-1-benzopyran-4-one. Tetrahydrofuran and acetic acid are used instead of dioxan/ethanol and sulphuric acid. The resulting oil crystallizes to give 3,4-dihydro-7,8-dihydroxy-3-(3-chlorophenyl)-2H-1-benzopyran, m.p. 99°–101°.

The starting materials are prepared as follows:

(a) As example 8, but using 2,3,4-trihydroxyphenyl-3'-chlorobenzylketone instead of 2,4,5-trihydroxyphenyl-4'-methylbenzylketone. 7,8-Dihydroxy-3-(3-chlorophenyl)-4H-1-benzopyran-4-one is obtained, m.p. 258°.

(b) As example 1, but using pyrogallol instead of 1,2,4-trihydroxybenzene and 3-chlorophenylacetonitrile instead of 4-methylphenylacetonitrile. 2,3,4-Trihydroxyphenyl-3'-chlorobenzylketone is obtained, m.p. 155°.

EXAMPLE 56

As example 40, but using 7,8-dihydroxy-3-(4-fluorophenyl)-4H-1-benzopyran-4-one (1.2 g) instead of 6,7-dihydroxy-3-(4-fluorophenyl)-4H-1-benzopyran-4-one. After evaporation of the filtrate, the residue is washed with water, dried under vacuum and then purified by elution on a silica gel column (CH$_2$Cl$_2$) to give 3,4-dihydro-7,8-dihydroxy-3-(4-fluorophenyl)-2H-1-benzopyran, m.p. 166°–168°.

The starting materials are prepared as follows:

(a) As example 8, but using 2,3,4-trihydroxyphenyl-4'-fluorobenzylketone instead of 2,4,5-trihydroxyphenyl-4'-methylbenzylketone. 7,8-Dihydroxy-3-(4-fluorophenyl)-4H-1-benzopyran-4-one is obtained, m.p. 289°.

(b) As example 1, but using pyrogallol instead of 1,2,4-trihydroxybenzene and 4-fluorophenylacetonitrile instead of 4-methylphenylacetonitrile. 2,3,4-Trihydroxyphenyl-4'-fluorobenzylketone is obtained, m.p. 152°.

EXAMPLE 57

As example 39, but using 6,7-methylenedioxy-3-(4-hydroxyphenyl)-4H-1-benzopyran-4-one [see Example 17] (1.2 g) instead of 6,7-dihydroxy-3-(3-methylphenyl)-4H-1-benzopyran-4-one. The resulting oil crystallizes to give 3,4-dihydro-6,7-methylenedioxy-3-(4-hydroxyphenyl)-2H-1-benzopyran, m.p. 139°–140°.

EXAMPLE 58

As example 39, but using 6,7-dihydroxy-3-(4-isopropylphenyl)-4H-1-benzopyran-4-one (1.2 g) instead of 6,7-dihydroxy-3-(3-methylphenyl)-4H-1-benzopyran-4-one. The resulting oil crystallizes to give 3,4-dihydro-6,7-dihydroxy-3-(4-isopropylphenyl)-2H-1-benzopyran, m.p. 129°–131°.

The starting materials are prepared as follows:

(a) As example 8, but using 2,4,5-trihydroxyphenyl-4'-isopropylbenzylketone instead of 2,4,5-trihydroxyphenyl-4'-methylbenzylketone. 6,7-Dihydroxy-3-(4-isopropylphenyl)-4H-1-benzopyran-4-one is obtained, m.p. 181°–182°.

(b) An example 1, but using 4-isopropylphenylacetonitrile instead of 4-methylphenylacetonitrile. 2,4,5-Trihydroxyphenyl-4'-isopropylbenzylketone is obtained, m.p. 131°.

EXAMPLE 59

As example 39, but using 6,7-dihydroxy-3-(4-carboxymethylphenyl)-4H-1-benzopyran-4-one (1.2 g) instead of 6,7-dihydroxy-3-(3-methylphenyl)-4H-1-benzopyran-4-one. The resulting oil crystallizes to give 3,4-dihydro-6,7-dihydroxy-3-(4-ethoxy-carbonylmethylphenyl)-2H-1-benzopyran, m.p. 164°–166°.

The starting materials are prepared as follows:

(a) 6,7-Dihydroxy-3-(4-cyanomethylphenyl)-4H-1-benzopyran-4-one (1 g) is dissolved in a mixture of conc. hydrochloric acid and acetic acid 1:1 (10 ml), then the solution is boiled for 2 h. After evaporation of the solution under vacuum and crystallization of the residue in a mixture of ethanol and water, 6,7-dihydroxy-(3-(4-carboxymethylphenyl)-4H-1-benzopyran-4-one is obtained, m.p. 278°–280°.

(b) As example 8, but using 2,4,5-trihydroxyphenyl-4'-cyanomethylbenzylketone instead of 2,4,5-trihydroxyphenyl-4'-methylbenzylketone. 6,7-Dihydroxy-3-(4-cyanomethylphenyl)-4H-1-benzopyran-4-one is obtained, m.p. 258°–260°.

(c) As example 1, but using 4-cyanomethylphenylacetonitrile instead of 4-methylphenylacetonitrile. 2,4,5-Trihydroxyphenyl-4'-cyanomethylbenzylketone is obtained, m.p. 195°–196°.

EXAMPLE 60

As example 39, but using 6,7-dihydroxy-3-(4-phenylsulfonylaminophenyl)-4H-1-benzopyran-4-one (1.2 g) instead of 6,7-dihydroxy-3-(3-methylphenyl)-4H-1-benzopyran-4-one. The resulting oil crystallizes to give 3,4-dihydro-6,7-dihydroxy-3-(4-phenylsulfonylaminophenyl)-2H-1-benzopyran, m.p. 152°–154°.

The starting material is prepared as follows:

(a) 6,7-Dihydroxy-3-(4-aminophenyl)-4H-1-benzopyran-4-one [see Example 51a] (538 mg) is dissolved in a mixture of dimethylformamide and water 15:85 (5 ml) and the solution is heated to 90° in the presence of benzenesulfonyl chloride (210 mg). After 15 minutes the pH has dropped to 3 and it is adjusted to 9 by addition of a 25% sodium hydroxide solution. Benzenesulfonyl chloride (additional 143 mg) and 25% sodium hydroxide solution (total amount used: 1 ml) are added in the same way until the pH does not vary any more. Aqueous hydrochloric acid is then added to lower the pH to 3 and the solution is cooled until precipitation occurs. The precipitate is filtered, washed with water and dried to give 6,7-dihydroxy-3-(4-phenylsulfonylaminophenyl)-4H-1-benzopyran-4-one, m.p. 285°–286°.

EXAMPLE 61

As example 40, but using 6,7-dihydroxy-3-(3-ethoxycarbonylphenyl)-4H-1-benzopyran-4-one (1.2 g) instead of 6,7-dihydroxy-3-(4-fluorophenyl)-4H-1-benzopyran-4-one. After evaporation of the filtrate, the residue crystallizes to give 3,4-dihydro-6,7-dihydroxy-3-(3-ethoxycarbonylphenyl)-2H-1-benzopyran, m.p. 131°–133°.

The starting materials are prepared as follows:

(a) As example 8, but using 2,4,5-trihydroxyphenyl-3'-ethoxycarbonylbenzylketone instead of 2,4,5-trihydroxyphenyl-4'-methylbenzylketone. After purification by column chromatography (silica gel/toluene:methanol 100:5), 6,7-dihydroxy-3-(3-ethoxycarbonylphenyl)-4H-1-benzopyran-4-one is obtained, m.p. 217°–218°.

(b) As example 1, but using 3-ethoxycarbonylphenylacetonitrile instead of 4-methylphenylacetonitrile. After purification by column chromatography (silica gel/methylene chloride:methanol 20:1) and crystallization from a mixture of methanol and water, 2,4,5-trihydroxyphenyl-3'-ethoxycarbonylbenzylketone is obtained, m.p. 177°–178°.

EXAMPLE 62

As example 39, but using 6,7-dihydroxy-3-(4-acetylaminophenyl)-4H-1-benzopyran-4-one (1.2 g) instead of 6,7-dihydroxy-3-(3-methylphenyl)-4H-1-benzopyran-4-one. The resulting oil crystallizes to give 3,4-dihydro-6,7-dihydroxy-3-(4-acetylaminophenyl)-2H-1-benzopyran, m.p. 201°–203° (88% purity).

The starting material is prepared as follows:

(a) 7-Acetyloxy-6-hydroxy-3-(4-acetylaminophenyl)-4H-1-benzopyran-4-one [see Example 65a] (20 mg) is dissolved in a mixture of 1N aqueous hydrochloric acid and ethanol 1:1 (10 ml) and stirred during 12 h at room temperature. The solution is then extracted with dichloromethane, the dichloromethane layer is washed with water and evaporated to dryness under vacuum to give 6,7-dihydroxy-3-(4-acetylaminophenyl)-4H-1-benzopyran-4-one, m.p.>310° (dec.).

EXAMPLE 63

As example 39, but using 6,7-dihydroxy-3-(3-methylsulfonylphenyl)-4H-1-benzopyran-4-one instead of 6,7-dihydroxy-3-(3-methylphenyl)-4H-1-benzopyran-4-one. 3,4-Dihydro-6,7-dihydroxy-3-(3-methylsulfonylphenyl)-2H-1-benzopyran is obtained.

The starting materials are prepared as follows:

(a) As example 8, but using 2,4,5-trihydroxyphenyl-3'-methylsulfonylbenzylketone instead of 2,4,5-trihydroxyphenyl-4'-methylbenzylketone. 6,7-Dihydroxy-3-(3-methylsulfonylphenyl)-4-H-1-benzopyran-4-one is obtained.

(b). As example 1, but using 3-methylsulfonylphenylacetonitrile instead of 4-methylphenylacetonitrile. 2,4,5-Trihydroxyphenyl-3'-methylsulfonylbenzylketone is obtained.

EXAMPLE 64

As example 39, but using 6,7-dihydroxy-3-(3-tert-butylphenyl)-4H-1-benzopyran-4-one instead of 6,7-dihydroxy-3-(3-methylphenyl)-4H-1-benzopyran-4-one. 3,4-Dihydro-6,7-dihydroxy-3-(3-tertbutylphenyl)-2H-1-benzopyran is obtained.

The starting materials are prepared as follows:

(a) As example 8, but using 2,4,5-trihydroxyphenyl-3'-tert-butylbenzylketone instead of 2,4,5-trihydroxyphenyl-4'-methylbenzylketone. 6,7-Dihydroxy-3-(3-tert-butylphenyl)-4H-1-benzopyran-4-one is obtained.

(b) As example 1, but using 3-tert-butylphenylacetonitrile instead of 4-methylphenylacetonitrile, 2,4,5-Trihydroxyphenyl-3'-tert-butylbenzylketone is obtained.

EXAMPLE 65

As example 39, but using 7-acetyloxy-6-hydroxy-3-(4-acetylaminophenyl)-4H-1-benzopyran-4-one (20 mg) instead of 6,7-dihydroxy-3-(3-methylphenyl)-4H-1-benzopyran-4-one. The resulting oil crystallizes to give 3,4-dihydro-6,7-dihydroxy-3-(4-acetylaminophenyl)-2H-1-benzopyran, m.p. 201°–203° (88% purity).

The starting material is prepared as follows:

(a) 6,7-Dihydroxy-3-(4-aminophenyl)-4H-1-benzopyran-4-one [see Example 51a] (269 mg) is dissolved in ethanol (3 ml). Acetic anhydride (4 ml) is added and the solution heated to 70° for 2.5 h, then left overnight at room temperature. The resulting precipitate is filtered, washed with water and dried to give 7-acetyloxy-6-hydroxy-3-(4-acetylaminophenyl)-4H-1-benzopyran-4-one, m.p. 265°–266°.

EXAMPLE 66

As example 39, but using 7,8-dihydroxy-3-(4-acetylaminophenyl)-4H-1-benzopyran-4-one instead of 6,7-dihydroxy-3-(3-methylphenyl)-4H-1-benzopyran-4-one. 3,4-Dihydro-7,8-dihydroxy-3-(4-acetylaminophenyl)-2H-1-benzopyran is obtained.

The starting materials are prepared as follows:

(a) As in example 8, but using 2,3,4-trihydroxyphenyl-4'-acetylaminobenzylketone instead of 2,4,5-trihydroxyphenyl-4'-methylbenzylketone. 7,8-Dihydroxy-3-(4-acetylaminophenyl)-4H-1-benzopyran-4-one is obtained.

(b) As example 1, but using pyrogallol instead of 1,2,4-trihydroxybenzene and 4-acetylaminophenylacetonitrile instead of 4-methylphenylacetonitrile. 2,3,4-Trihydroxyphenyl-4'-acetylaminobenzylketone is obtained.

EXAMPLE 67

As example 39, but using 7,8-dihydroxy-3-(4-carbamoylphenyl)-4H-1-benzopyran-4-one instead of 6,7-dihydroxy-3-(3-methylphenyl)-4H-1-benzopyran-4-one. 3,4-Dihydro-7,8-dihydroxy-3-(1-benzopyran is obtained.

The starting materials are prepared as follows:

(a) As in example 8, but using 2,3,4-trihydroxyphenyl-4'-carbamoylbenzylketone instead of 2,4,5-trihydroxyphenyl-4'-methylbenzylketone. 7,8-Dihydroxy-3-(4-carbamoylphenyl)-4H-1-benzopyran-4-one is obtained.

(b) As example 1, but using pyrogallol instead of 1,2,4-trihydroxybenzene and 4-carbamoylphenylacetonitrile instead of 4-methylphenylacetonitrile. 2,3,4-Trihydroxyphenyl-4'-carbamoylbenzylketone is obtained.

EXAMPLE 68

As example 39, but using 7,8-dihydroxy-3-(3-n-propylsulfonylphenyl)-4H-1-benzopyran-4-one instead of 6,7-dihydroxy-3-(3-methylphenyl)-4H-1-benzopyran-4-one. 3,4-Dihydro-7,8-dihydroxy-3-(3-n-propylsulfonylphenyl)-2H-1-benzopyran is obtained.

The starting materials are prepared as follows:

(a) As example 8, but using 2,3,4-trihydroxyphenyl-3'-n-propylsulfonylbenzylketone instead of 2,4,5-trihydroxyphenyl-4'-methylbenzylketone. 7,8-Dihydroxy-3-(3-n-propylsulfonylphenyl)-4H-1-benzopyran-4-one is obtained.

(b) As example 1, but using pyrogallol instead of 1,2,4-trihydroxybenzene and 3-n-propylsulfonylphenylacetonitrile instead of 4-methylphenylacetonitrile. 2,3,4-Trihydroxyphenyl-3'-n-propylsulfonylbenzylketone is obtained.

EXAMPLE 69

As example 39, but using 7,8-dimethoxy-3-(3-carboxyphenyl)-4H-1-benzopyran-4-one instead of 6,7-dihydroxy-3-(3-methylphenyl)-4H-1-benzopyran-4-one. 3,4-Dihydro-7,8-dimethoxy-3-(3-carboxyphenyl)-2H-1-benzopyran is obtained.

The starting material is prepared as follows:

(a) As example 49a, but using 7,8-dihydroxy-3-(3-carboxyphenyl)-4H-1-benzopyran-4-one ]see Example 37a] instead of 7,8-dihydroxy-3-(4-methylphenyl)-4H-1-benzopyran-4-one. 7,8-Dimethoxy-3-(3-carboxyphenyl)-4H-1-benzopyran-4-one is obtained.

EXAMPLE 70

As example 39, but using 7,8-dimethoxy-3-(4-carboxymethoxyphenyl)-4H-1-benzopyran-4-one instead of 6,7-dihydroxy-3-(3-methylphenyl)-4H-1-benzopyran-4-one. 3,4-Dihydro-7,8-dimethoxy-3-(4-carboxymethoxyphenyl)-2H-1-benzopyran is obtained.

The starting material is prepared as follows:

(a) NaH is dissolved in dry dimethylformamide under nitrogen atmosphere at 0°. 7,8-Dimethoxy-3-(4-hydroxyphenyl)-4H-1-benzopyran-4-one [cp. J. Inst. Chem. (Calcutta) 43, 234 (1971)], dissolved in dry dimethylformamide, is added slowly, then a solution of chloroacetic acid. The solution is heated at 70° for 5 h and evaporated under vacuum to about one third of its original volume. After cooling, water is added and a precipitate occurs which is filtered and crystallized in methanol to give 7,8-dimethoxy-3-(4-carboxymethoxyphenyl)-4H-1-benzopyran-4-one.

EXAMPLE 71

As example 39, but using 7,8-methylenedioxy-3-(4-carboxyphenyl)-4H-1-benzopyran-4-one instead of 6,7-dihydroxy-3-(3-methylphenyl)-4H-1-benzopyran-4-one. 3,4-Dihydro-7,8-methylenedioxy-3-(4-carboxyphenyl)-2H-1-benzopyran is obtained.

The starting materials are prepared as follows:

(a) As example 8, but using 2-hydroxy-3,4-methylenedioxyphenyl-4'-carboxybenzylketone instead of 2,4,5-trihydroxyphenyl-4'-methylbenzylketone. 7,8-Methylenedioxy-3-(4-carboxyphenyl)-4H-1-benzopyran-4-one is obtained.

(b) As example 1, but using 2-hydroxy-3,4-methylenedioxybenzene instead of 1,2,4-trihydroxybenzene and 4-carboxyphenylacetonitrile instead of 4-methylphenylacetonitrile. 2-Hydroxy-3,4-methylenedioxyphenyl-4'-carboxybenzylketone is obtained.

I claim:

1. A compound of the formula I

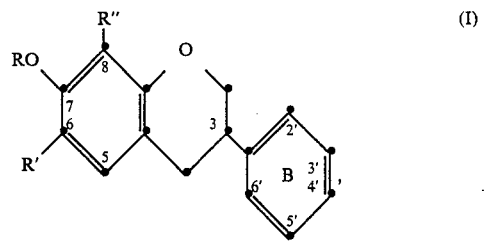

wherein the group OR represents hydroxy; lower alkoxy which is unsubstituted or substituted by hydroxy, lower alkoxy, amino, lower alkylamino, di-lower alkylamino, carboxy or lower alkoxycarbonyl; or lower alkanoyloxy; one of the radicals R' and R" represents hydroxy, lower alkoxy, lower alkanoyloxy or lower alkyl and the other one is hydrogen; or the groups OR and R' together form a bivalent methylenedioxy radical which is unsubstituted or substituted by lower alkyl and/or phenyl, and R" is hydrogen; or the groups OR and R" together form a bivalent methylenedioxy radical which is unsubstituted or substituted by lower alkyl and/or phenyl, and R' is hydrogen; and the ring B is unsubstituted or substituted by lower alkyl, phenyl-lower alkyl, diphenyl-lower alkyl, phenyl, lower alkanoyloxy, halogen, amino, lower alkylamino, di-lower alkylamino, phenylamino, lower alkanoylamino, benzoylamino; lower alkylsulfonylamino, phenylsulfonylmino; lower alkanoyl, benzoyl, carboxy, lower alkoxycarbonyl, carbamoyl, N-lower alkylcarbamoyl, N,N-dilower alkylcarbamoyl, cyano, ureido, N-lower alkylureido, lower alkylsulfonyl; phenylsulfonyl; lower alkyl which is substituted by hydroxy, lower alkoxy, amino, lower alkylamino, di-lower alkylamino, halogen, carboxy or lower alkoxycarbonyl; lower alkoxy which is substituted by hydroxy, lower alkoxy, amino, lower alkylamino, di-lower alkylamino, halogen, carboxy or lower alkoxycarbonyl; $C_3$–$C_7$-alkoxy; and/or bivalent methylenedioxy;

or wherein the ring B is monosubstituted by hydroxy, methoxy or ethoxy, provided that R' is other than hydroxy, methoxy or ethoxy, if the group OR represents hydroxy, methoxy or ethoxy; or wherein the ring B is disubstituted by methoxy and lower alkoxy, provided in case of 2',4'-dimethoxy substitution that R' and R" are other than methoxy, if the group OR represents methoxy; with the proviso that the ring B must be substituted, if R' is hydroxy and the group OR represents hydroxy or methoxy; it being possible for all phenyl groups mentioned as such or in composed radicals to be unsubstituted or substituted by lower alkyl, lower alkoxy, halogen, hydroxy and/or nitro; or a salt thereof.

2. A compound according to claim 1 of the formula I, wherein the group OR represents hydroxy, lower alkoxy or lower alkanoyloxy; one of the radicals R' and R" represents hydroxy, lower alkoxy, lower alkanoyloxy or lower alkyl and the other one is hydrogen; or the groups OR and R' together form a bivalent methylenedioxy radical which is unsubstituted or substituted by lower alkyl and/or phenyl, and R" is hydrogen; or the groups OR and R" together form a bivalent methylenedioxy radical which is unsubstituted or substituted by lower alkyl and/or phenyl, and R' is hydrogen; and the ring B is unsubstituted or substituted by lower alkyl, lower alkanoyloxy, halogen, amino, lower alkylamino, di-lower alkylamino, phenylamino, lower alkanoylmino, benzoylamino; lower alkylsulfonylamino, phenylsulfonylamino; lower alkanoyl, benzoyl, carboxy, lower alkoxycarbonyl, carbamoyl, N-lower alkylcarbamoyl, N,N-di-lower alkylcarbamoyl, cyano, lower alkylsulfonyl; phenylsulfonyl; lower alkyl which is substituted by halogen, carboxy or lower alkoxycarbonyl; lower alkoxy which is substituted by carboxy or lower alkoxycarbonyl; or bivalent methylenedioxy;

or wherein the ring B is monosubstituted by hydroxy or methoxy, provided that R' is other than hydroxy, methoxy or ethoxy, if the group OR represents hydroxy, methoxy or ethoxy; or wherein the ring B is disubstituted by methoxy, provided in case of 2',4'-dimethoxy substitution that R' and R" are other than methoxy, if the group OR represents methoxy; with the proviso that the ring B must be substituted, if R' is hydroxy and the group OR represents hydroxy or methoxy; or a pharmaceutically acceptable salt thereof.

3. A compound according to claim 1 of the formula I, wherein the group OR represents hydroxy, lower alkoxy or lower alkanoyloxy; one of the radicals R' and R" represents hydroxy, lower alkoxy, lower alkanoyloxy or lower alkyl and the other one is hydrogen; or the groups OR and R' together form a bivalent methylenedioxy radical which is unsubstituted or disubstituted by phenyl, and R" is hydrogen; or the groups OR and R" together form a bivalent methylenedioxy radical which is unsubstituted or disubstituted by phenyl, and R' is hydrogen; and the ring B is unsubstituted or substituted by lower alkyl, lower alkanoyloxy, halogen, amino, lower alkanoylamino, phenylsulfonylamino; carboxy, lower alkoxycarbonyl, carbamoyl, lower alkylsulfonyl; lower alkyl which is substituted by halogen or carboxy; lower alkoxy which is substituted by carboxy or lower alkoxycarbonyl; or bivalent methylenedioxy;

or wherein the ring B is monosubstituted by hydroxy or methoxy, provided that R' is other than hydroxy, methoxy or ethoxy, if the group OR represents hydroxy, methoxy or ethoxy; or wherein the ring B is disubstituted by methoxy, provided in case of 2',4'-dimethoxy substitution that R' and R" are other than methoxy, if the group OR represents methoxy; with the proviso that the ring B must be substituted, if R' is hydroxy and the group OR represents hydroxy or methoxy; or a pharmaceutically acceptable salt thereof.

4. A compound according to claim 1 of the formula I, wherein the group OR represents hydroxy; lower alkoxy or lower alkanoyloxy; one of the radicals R' and R" represents hydroxy, lower alkoxy, lower alkanoyloxy or lower alkyl and the other one is hydrogen; or the groups OR and R' together form a bivalent methylenedioxy radical which is unsubstituted or disubstituted by phenyl, and R" is hydrogen; or the groups OR and R" together form a bivalent methylenedioxy radical which is unsubstituted or disubstituted by phenyl, and R' is hydrogen; and the ring B is unsubstituted or substituted by lower alkyl, lower alkanoyloxy, halogen, amino, lower alkylamino, di-lower alkylamino, or lower alkoxy which is substituted by carboxy or lower alkoxycarbonyl; or ring B is 3,4-dimethoxy-substituted; with the proviso that the ring B must be substituted, if R' is hydroxy and the group OR represents hydroxy or methoxy; or a pharmaceutically acceptable salt thereof.

5. A compound according to claim 1 being 3,4-dihydro-6,7-dihydroxy-3-(3,4-dimethoxyphenyl)-2H-1-benzopyran.

6. A compound according to claim 1 being 3,4-dihydro-7,8-dihydroxy-3-(3,4-dimethoxyphenyl)-2H-1-benzopyran.

7. A compound according to claim 1 being 3,4-dihydro-6,7-dihydroxy-3-(4-methylphenyl)-2H-1-benzopyran.

8. A compound according to claim 1 being 3,4-dihydro-6,7-diphenylmethylenedioxy-3-(4-methoxyphenyl)-2H-1-benzopyran.

9. A compound according to claim 1 being 3,4-dihydro-6,7-diacetoxy-3-(4-methoxyphenyl)-2H-1-benzopyran.

10. A pharmaceutical composition comprising a therapeutically effective amount of a compound of formula I according to claim 1 or a pharmaceutically acceptable salt thereof, together with one or more pharmaceutically acceptable carriers.

11. A pharmaceutical composition according to claim 10, wherein it contains 3,4-dihydro-6,7-dihydroxy-3-(4-methylphenyl)-2H-1-benzopyran together with one or more pharmaceutically acceptable carriers.

12. A method of treating a vascular disease responsive to platelet aggregation inhibition in a mammal comprising the administration to said mammal of a therapeutically effective amount of a compound of formula I according to claim 1 or a pharmaceutically acceptable salt thereof.

13. A method according to claim 12 wherein 3,4-dihydro-6,7-dihydroxy-3-(4-methylphenyl)-2H-1-benzopyran is administered.

* * * * *